US007674772B2

(12) United States Patent
Kim

(10) Patent No.: US 7,674,772 B2
(45) Date of Patent: Mar. 9, 2010

(54) COMPOSITIONS AND METHODS FOR TREATING ATHEROSCLEROSIS

(75) Inventor: Perry M. Kim, Inverary (CA)

(73) Assignee: Queen's University at Kingston, Kingston, Ontario (CA)

( * ) Notice: Subject to any disclaimer, the term of this patent is extended or adjusted under 35 U.S.C. 154(b) by 0 days.

(21) Appl. No.: 11/693,820

(22) Filed: Mar. 30, 2007

(65) Prior Publication Data

US 2007/0232545 A1 Oct. 4, 2007

Related U.S. Application Data

(60) Provisional application No. 60/788,516, filed on Mar. 31, 2006.

(51) Int. Cl.
*A61K 38/10* (2006.01)
*C07K 7/08* (2006.01)

(52) U.S. Cl. ........................................ 514/13; 530/326

(58) Field of Classification Search ....................... None
See application file for complete search history.

(56) References Cited

U.S. PATENT DOCUMENTS

| | | | | |
|---|---|---|---|---|
| 5,318,958 A | 6/1994 | Kisilevsky | ................... | 514/21 |
| 5,700,909 A * | 12/1997 | O'Brien | ...................... | 530/326 |
| 5,789,382 A | 8/1998 | Wellstein | ..................... | 514/14 |
| 6,004,936 A | 12/1999 | Kisilevsky | ................... | 514/21 |
| 6,261,569 B1 | 7/2001 | Comis et al. | ............. | 424/204.1 |
| 6,458,357 B1 | 10/2002 | White et al. | ............. | 424/185.1 |
| 7,291,590 B2 | 11/2007 | Kisilevsky et al. | ............. | 514/2 |
| 2004/0265982 A1 * | 12/2004 | Kisilevsky et al. | .......... | 435/197 |
| 2006/0111299 A1 | 5/2006 | Kisilevsky et al. | ............ | 514/14 |

FOREIGN PATENT DOCUMENTS

| | | |
|---|---|---|
| CA | 2 531 890 | 12/2004 |
| WO | WO 96/38166 | 12/1996 |
| WO | WO 00/77029 | 12/2000 |
| WO | WO 01/21188 A1 | 3/2001 |
| WO | WO 02/43742 | 6/2002 |
| WO | WO 2004/111084 A2 | 12/2004 |

OTHER PUBLICATIONS

Ancsin et al., "Basic residues in the Carboxy-Terminus of Mouse apoSAA are Involved in Heparin Binding", Proceedings of the VIIIth International Symposium on Amyloidosis, Rochester, Minnesota, USA Aug. 7-11, 1998 published in *Amyloid and Amyloidosis* 1998, Kyle, R.A. and Gertz, M.A., (eds.) Parthenon Publishing Group Limited, New York (1999), p. 17-19.

(Continued)

*Primary Examiner*—Jeffrey E Russel
(74) *Attorney, Agent, or Firm*—Licata & Tyrrell P.C.

(57) ABSTRACT

Reverse peptides and mimetics of a mammalian serum amyloid A isoform 2.1 (SAA2.1) domain or a portion thereof and compositions and pharmaceutical compositions thereof are provided that enhance the effect on macrophage cholesterol ester hydrolase activity. Methods of using these reverse peptides, mimetics thereof and compositions in the treatment and/or prevention of atherosclerosis as well as coronary heart disease and cardiovascular disease are also provided.

27 Claims, 1 Drawing Sheet

60
40
20
0
dpm/μl plasma
*
Control
Reversed D-19mer

OTHER PUBLICATIONS

Ancsin et al., "Studies Defining the Serum Amyloid A:Heparin Binding Sites" FASEB Summer Conference, Copper Mountain Colorado, Jun. 11-16, 2000 (Abstract).
Ancsin et al., "The Heparin/Heparan Sulfate-binding Site on Apo-serum Amyloid A", J. Biol. Chem 1999 274:7172-7181.
Ancsin et al., "Laminin interactions with the apoproteins of acute-phase HDL:preliminary mapping of the laminin binding site on serum amyloid A", Amyloid: Int. J. Exp. Clin. Invest. 1999 6:37-47.
Bagshaw et al., "Characteristics of SAA-Phosphatidylcholine (PC) Liposome Binding to Mouse Macrophages", Canadian Federation of Biological Sciences, Montreal, Quebec, Jun. 1994 (Abstract).
Banka et al., "Serum amyloid A (SAA) :influence on HDL-mediated cellular cholesterol efflux", J. Lipid Res. 1995 36:1058-1065.
Bays et al., "Pharmacotherapy for dyslipidaemia -current therapies and future agents", Expert Opinion on Pharmacotherapy 2003 4(11):1901-1938.
Delsing et al., "Differential Effects of Amlodipine and Atorvastatin Treatment and Their Combination on Atherosclerosis in ApoE*3-Leiden Transgenic Mice", J. Cardiovasc. Pharmacol. 2003 42(1):63-70.
Ely et al., "The in-vitro influence of serum amyloid A isoforms on enzymes that regulate the balance between esterified and un-esterified cholesterol", Amyloid J. Protein Folding Disord. 2001 8:169-181.
Ely et al., "Influence of Serum Amyloid A (SAA) on Macrophage AcylCoA:Cholesterol Acyltransferase (ACAT) activity", VIIIth International Amyloid Symposium, Rochester, Minnesota, U.S.A., Aug. 7-11, 1998 published in *Amyloid and Amyloidosis 1998*, Kyle, R.A. and Gertz, M.A. (eds.) Parthenon Publishing Group Limited, New York (1999), p. 366-368.
Ganji et al., "Niacin and cholesterol:role in cardiovascular disease (Review)", J. Nutritional Biochemistry 2003 14:298-305.
Jousilahti et al., "The association of c-reactive protein, serum amyloid a and fibrinogen with prevalent coronary heart disease-baseline findings of the PAIS project", Atherosclerosis 2001 156:451-456.
Kajinami et al., "Cholesterol absorption inhibitors in development as potential therapeutics", Expert Opinion Investig. Drugs 2002 11(6):831-835.
Kinkley et al. "An EM autoradiography and Immunofluorescence Study Examining the Pathway of Serum Amyloid A Through the Macrophage", Xth International Amyloid Symposium, Tours, France, Apr. 18-22, 2004 (Abstract).
Kinkley et al. "An EM Autoradiography and Immunofluorescence Study Examining the Pathway of Serum Amyloid A Through the Macrophage", Xth International Amyloid Symposium, Tours, France, Apr. 18-22, 2004.
Kisilevsky et al. "Macrophage cholesterol efflux and the active domains of serum amyloid A 2.1", J. Lipid Res. 2003 44: 2257-2269.
Kisilevsky et al. "Serum Amyloid A (SAA) Changes HDL's Cellular Affinity: A Clue to SAA's Principal Function". 81st Annual Meeting U.S.-Canadian Academy of Pathology, Atlanta, Georgia, U.S.A. Mar. 1992, Abstract published in Lab. Invest. 1992 66:107A, (Abstract).
Kisilevsky et al. "Serum Amyloid A Influences the Efflux of Cholesterol from Macrophages", VIIth International Symposium on Amyloidosis, Kingston, Ontario, Canada, Jul. 1993 pp. 115-118.
Kisilevsky et al., "Influence of Serum Amyloid A (SAA) on Macrophage Acyl-CoA:Cholesterol Acyltransferase (ACAT) Activity". 52$^{nd}$ Annual Meeting of the Canadian Cardiovascular Society, Quebec City, Quebec, Canada, Oct. 19-23, 1999 published in *Can. J. Cardiol. 1999* 15(Suppl D): 209D (Abstract).
Kisilevsky et al., "The Mechanism of Serum Amyloid A's (SAA) Stimulation of Neutral Cholesterol Ester Hydrolase (NCEH) Activity". 52$^{nd}$ Annual Meeting of the Canadian Cardiovascular Society, Quebec City, Quebec, Canada, Oct. 19-23, 1999 published in *Can. J. Cardiol. 1999* 15(Suppl D): 180D (Abstract).
Kisilevsky et al., "Promoting Cholesterol Export from Macrophage Foam Cells—the Mechanism of Action of SAA2.1 and Its Implications". Canadian Cardiovascular Congress, Oct. 26-30, 2002, Edmonton, Alberta, Canada (Abstract).
Kisilevsky et al., "The promotion of macrophage cholesterol efflux by active domains of serum amyloid 2.1". Canadian Lipoprotein Conference, Muskoka, Ontario, Canada, Oct. 23-25, 2003 (Abstract).
Kisilevsky et al., "Acute Phase Serum Amyloid A, Cholesterol Metabolism, and Cardiovascular Disease", Pediatric Pathology and Molecular Medicine 2002 21:291-305.
Kisilevsky, R., "Serum Amyloid A (SAA), a Protein without a Function:Some Suggestions with Reference to Cholesterol Metabolism", Medical Hypotheses 1991 35:337-341.
Kisilevsky et al., "Acute phase serum amyloid A (SAA) and cholesterol transport during acute inflammation:A hypothesis", Amyloid: Int. J. Exp. Clin. Invest. 1996 3:252-260.
Kisilevsky et al., "Serum amyloid A changes high density lipoprotein's cellular affinity:A Clue to Serum Amyloid A's Principal Function", Laboratory Investigation 1992 66:778-785 with attached Erratum (Kisilevsky et al., Laboratory Investigation 1992 67:151.
Knopp, R.H., "Evaluating Niacin in its Various Forms", Am. J. Cardiol. 2000 86(supp):51L-56L.
Kumon et al., "A Longitudinal Analysis of Alteration in Lecithin-Cholesterol Acyltransferase and Paraoxonase Activities Following Laparoscopic Cholecystectomy Relative to Other Parameters of HDL Function and the Acute Phase Response", Scand. J. Immunol. 1998 48:419-424.
Lee et al., "Minireview:Lipid Metabolism, Metabolic Diseases, and Peroxisome Proliferator-Activated Receptors", Endocrinology 2003 144:2201-2207.
Liang et al., "Serum Amyloid A Is a Chemotactic Agonist at FPR2, a Low-Affinity *N*-Formylpeptide Receptor on Mouse Neutrophils", Biochem. Biophys. Res. Commun 2000 270: 331-335.
Liang et al., "Recombinant human serum amyloid A ($apoSAA_p$) binds cholesterol and modulates cholesterol flux", J. Lipid Res. 1995 36:37-46.
Liang et al., "Amino terminal region of acute phase, but not constitutive, serum amyloid A (apoSAA) specifically binds and transports cholesterol into aortic smooth muscle and HepG2 cells", J. Lipid Res. 1996 37:2109-2116.
Lindhorst et al., "Acute inflammation, acute phase serum amyloid A and cholesterol metabolism in the mouse", Biochimica et Biophysica Acta 1997 1339:143-154.
Liuzzo et al., "The Prognostic Value of C-Reactive Protein and Serum Amyloid A Protein in Severe Unstable Angina", N. Engl. J. Med. 1994 331:417-424.
McCarthy et al., "Potent, Selective, and Systemically-Available Inhibitors of Acyl-Coenzyme A:Cholesterol Acyl Transferase (ACAT)", J. Med. Chem. 1994 37:1252-1255.
Ridker et al., "Inflammation, Pravastatin, and Risk of Coronary Events After Myocardial Infarction in Patients With Average Cholesterol Levels", Circulation 1998 98:839-844.
Robinson et al., "Use of Niacin in the Prevention and Management of Hyperlipidemia", Prog. Cardiovasc. Nurs. 2001 16(1):14-20.
Röcken et al., "Binding and endocytosis of $HDL_{SAA}$ by macrophages: implications for the pathogenesis of AA-amyloidosis?", German Society of Pathology, Dresden, Germany, Jun. 1996 (Abstract).
Röcken et al., "Binding and endocytosis of murine high density lipoprotein from healthy (HDL) and inflamed donors ($HDL_{SAA}$) by murine macrophages in vitro. A light and electromicroscopic investigation", Amyloid:Int. J. Exp. Clin. Invest. 1997 4:259-273.
Röcken et al., Comparison of the binding and endocytosis of high-density lipoprotein from healthy (HDL) and inflamed ($HDL_{SAA}$) donors by murine macrophages of four different mouse strains. *Virchows Arch* 1998 432(6): 547-555.
Rosenthal et al., "Variation with Age and Disease of an Amyloid A Protein-Related Serum Component", J. Clin. Invest. 1975 55:746-753.
Shah et al., "Effects of Recombinant Apolipoprotein A-$I_{Milano}$ on Aortic Atherosclerosis in Apolipoprotein E-Deficient Mice", Circulation 1998 97:780-785.
Steinmetz et al., "Influence of serum amyloid A on cholesterol esterification in human plasma", Biochimica et Biophysica Acta 1989 1006:173-178.

Su et al., "A seven-transmembrane, G protein-coupled Receptor, FPRL1, Mediates the Chemotactic Activity of Serum Amyloid A for Human Phagocytic Cells". J. Exp. Med. 1999 189:395-402.
Tam et al., "Promoting export of macrophage cholesterol:the physiological role of a major acute-phase protein, serum amyloid A 2.1", J. Lipid Research 2002 43:1410-1420.
Tam et al., "Influence of Murine Serum Amyloid A 2.1, and its Active Domains, on Human Macrophage Cholesterol Export in Cell Culture", Xth International Amyloid Symposium, Tours, France, Apr. 18-22, 2004 (Abstract).
Tam et al. "Influence of Murine Serum Amyloid A 2.1, and its Active Domains, on Human Macrophage Cholesterol Export in Cell Culture", Xth International Amyloid Symposium, Tours, France, Apr. 18-22, 2004.
Tam et al. "Structural Aspects of the Active Domain of Murine and Human Serum Amyloid A 2.1 Responsible for its ACAT Inhibitory Properties", Xth International Amyloid Symposium, Tours, France, Apr. 18-22, 2004 (Abstract).
Tam et al., "The physiological role of serum amyloid A 2.1". IXth International Amyloid Symposium, Budapest, Hungary, Jul. 15-21, 2001, Abstract published in Amyloid J. Protein Folding Disord. 2001 8: Suppl 2:21-22 (Abstract).
Tam et al., "In Vivo Influence of Serum Amyloid A 2.1 and its Active Domains on Macrophage Cholesterol Export", Xth International Amyloid Symposium, Tours, France, Apr. 18-22, 2004 (Abstract).
Tam et al., "In Vivo Influence of Serum Amyloid A 2.1 and its Active Domains on Macrophage Cholesterol Export", Xth International Amyloid Symposium, Tours, France, Apr. 18-22, 2004.
Tontonoz et al., "Liver X Receptor Signaling Pathways in Cardiovascular Disease", Molecular Endocrinology 2003 17:985-993.
Van Lenten et al., "Anti-inflammatory HDL Becomes Pro-inflammatory during the Acute Phase Response", J. Clin. Invest. 1995 96:2758-2767.
Van et al., "Comparison of Extended-Release Niacin and Atorvastatin Monotherapies and Combination Treatment of the Atherogenic Lipid Profile in Diabetes Mellitus", Am. J. Cardiol. 2002 89(11):1306-1308.
Young et al., "SAA Inhibits HDL-Cholesterol Uptake from LDL/VLDL: An Additional Clue to Its Principal Function". 84th Annual Meeting US-Canadian Academy of Pathology, Toronto, Ontario, Canada, Mar. 1995, Abstract published in Lab. Invest. 72: 37A, 1995 (Abstract).
UnitProt Accession No. Q9XSG7 Nov. 1, 1999.
Sela et al., "Different roles of D-amino acids in immune phenomena", FASEB J. 11:449-456 1997.
Tam et al., "Peptides derived from serum amyloid A prevent, and reverse, aortic lipid lesions in apoE$^{-/-}$ mice", J. Lipid Res. 2005 46:2091-2101.
Arcoleo et al., "Effect of partially modified retro-inverso analogues derived from C-reactive protein on the induction of nitric oxide synthesis in peritoneal macrophages", British Journal of Pharmacology 1997 120:1383-1389.
Fischer, P.M., "The design, synthesis and application of stereochemical and directional peptide isomers:a critical review", Current Protein and Peptide Science 2003 4:339-356.
Guptasarma, P., "Reversal of peptide backbone direction may result in the mirroring of protein structure", FEBS 1992 310(3):205-210.
Kinkley et al., "The path of murine serum amyloid a through peritoneal macrophages" Amyloid 2006 13(3):123-134.
Manley et al., "Rapid recycling of cholesterol:the joint biologic role of C-reactive protein and serum amyloid A", Medical Hypotheses 2006 66:784-792.
Manley et al., "Rapid and efficient recycling of cholesterol:the joint biological role of C-reactive protein and serum amyloid A", Canadian Association of Pathologists, St. John's, Newfoundland, Canada, Jul. 2006 Abstract.
Rudinger et al., "Characteristics of the amino acids as components of a peptide hormone sequence", Peptide Hormones, University Park Press, Baltimore, MD pp. 1-7.
Bowie et al., "Deciphering the message in protein sequences:tolerance to amino acid substitutions", Science 1990 247:1306-1310.
U.S. Appl. No. 11/872,309, filed Oct. 15, 2007, Kisilevsky et al.
Liu et al., "Cyclodextrins differentially mobilize free and esterified cholesterol from primary human foam cell macrophages", Journal of Lipid Research 2003 44:1156-1166.

* cited by examiner

COMPOSITIONS AND METHODS FOR TREATING ATHEROSCLEROSIS

This patent application claims the benefit of priority from U.S. Provisional Application Ser. No. 60/788,516, filed Mar. 31, 2006, teachings of which are herein incorporated by reference in their entirety.

FIELD OF THE INVENTION

The present invention relates to synthetic reverse peptides of a macrophage cholesterol ester hydrolase enhancing domain of mammalian serum amyloid A isoforms 2.1 (SAA2.1) and 1.1 (SAA1.1) or a portion thereof. These reverse peptides, mimetics thereof or compositions containing these reverse peptides or mimetics thereof, and pharmaceutical compositions comprising one or more of these reverse peptides, mimetics thereof or compositions, are useful in inhibiting the storage of cholesterol and potentiating the mobilization and release of cholesterol from inflammatory or atherosclerotic sites in a subject. The reverse peptides and mimetics thereof, and the compositions and pharmaceutical compositions thereof, are useful in the treatment and/or prevention of atherosclerosis and inflammation, as well as coronary heart disease and cardiovascular disease.

BACKGROUND OF THE INVENTION

Multiple studies have been conducted with reverse sequences of D amino acid peptides, sometimes referred to as retro-inversal (also known as retro-inverso, retro-enantio, retro-all) D amino acid peptides, with varying results.

For example, a reverse L amino acid and a retro-inversal D amino acid peptide having similar activity to its native forward L amino acid or D amino acid peptide are disclosed by Guo et al. (J. Pept. Res. 1997 50(3):210-221 and J. Immunol 2002 169:2180-2188) and Shafiee et al. (Invest. Ophthalmol. Vis. Sci. 2000 41: 2378-2388). Specifically, Guo et al. (J. Pept. Res. 1997 50:210-221) showed that a retro-inverso peptide had similar anti-tumor activity to the native forward peptide. Shafiee et al. (Invest. Ophthalmol. Vis. Sci. 2000, 41: 2378-2388) showed that certain D amino acid peptides were approximately two times more potent than their corresponding forward L amino acid peptides at inhibiting retinal angiogenesis in a retinal explant assay.

However, reverse peptides do not always exhibit similar efficacy to their corresponding forward peptide. Nor do they necessarily bind to the same catalytic or receptor site within or on an enzyme or protein as their corresponding forward peptide. For example, Zhou et al. (JBC 2002 277:17476-17485) showed that a retro-inversal D amino acid peptide, which corresponds to a protein located on the HIV virus, binds to the CXCR4 chemokine receptor, but acts as an antagonist to the natural HIV protein ligand. Buchet et al. (Biochem. Biophys. Acta 1996 1315:40-46) showed that the retro-inversal peptide of Aβ[35-25] altered the aggregation properties of the natural Aβ[25-35] peptide (i.e. random coil structure vs. β-sheet structure). Hwang et al. (Biochem. J. 2006 395:165-172) showed that the reverse L amino acid peptide of NSA9, a peptide derived from human prothrombin kringle-2, and NSA7, a truncated form of NSA9, did not have the same anti-proliferative effects as the natural L amino acid peptides.

SUMMARY OF THE INVENTION

A selected peptide domain of mammalian serum amyloid A isoforms 2.1 (SAA2.1) and 1.1 (SAA1.1) and portions thereof and mimetics thereof have been demonstrated to have a potent enhancing effect on macrophage cholesterol ester hydrolase (CEH) activity. As shown herein, reverse peptides of this domain, or a portion thereof, also have a potent enhancing effect on CEH activity. Reverse peptides of this domain or a portion thereof shift macrophage cholesterol into a transportable form that is then rapidly exported from the cell in the presence of a cholesterol transporter and a cholesterol acceptor, high density lipoprotein (HDL). Thus, these reverse peptides and mimetics thereof, more preferably retro-inversal D amino acid peptides and mimetics thereof, are useful in methods of inhibiting the storage of cholesterol and potentiating the mobilization and release of cholesterol from inflammatory or atherosclerotic sites in a subject. Further, these reverse peptides and mimetics thereof, more preferably retro-inversal D amino acid peptides and mimetics thereof, are effective at regressing and/or decreasing formation of arterial atherosclerotic lesions and treating or preventing atherosclerosis, cardiovascular disease, coronary heart disease and inflammation in a subject.

Accordingly, the present invention provides reverse peptides of the CEH enhancing domain of SAA2.1 or SAA1.1 or a portion thereof, mimetics of these reverse peptides, and compositions comprising these reverse peptides or mimetics thereof, as well as pharmaceutical compositions comprising these reverse peptides, mimetics thereof, or compositions, and methods for use of these reverse peptides, mimetics thereof, compositions, and pharmaceutical compositions to modulate the activity of the macrophage cholesterol metabolizing enzyme CEH.

One aspect of the present invention relates to a reverse peptide, a peptide variant, or a mimetic thereof of the CEH enhancing domain of SAA proteins or a portion thereof. CEH enhancing domains have been identified as residing in residues 74-103 of the C-terminus of murine SAA2.1, residues 77-103 of the C-terminus of murine SAA1.1, and 78-104 of the C-terminus of human SAA1.1 and SAA2.1. Preferred reverse peptides or mimetics thereof capable of enhancing cholesterol ester hydrolase activity include a synthetic peptide or a mimetic thereof comprising a formula $X_{18}X_{17}X_{16}X_{15}X_{14}X_{13}X_{12}X_{11}X_{10}X_9X_8X_7X_6X_5X_4X_3X_2X_1$ (SEQ ID NO:1) or a portion thereof wherein $X_1$ and $X_9$, $X_{12}$ or $X_{18}$ are amino acids capable of forming a salt bridge, $X_6$ is glutamic acid or lysine or an amino acid which is a conservative substitution thereof, and $X_2$, $X_3$, $X_4$, $X_5$, $X_7$, $X_8$, $X_{10}$, $X_{11}$, $X_{13}$, $X_{14}$, $X_{15}$, $X_{16}$, and $X_{17}$ are independently any amino acid. Preferred is a reverse peptide comprising RFHNPDKGSRGWENAAQDA (SEQ ID NO:2) or a portion thereof. More preferred is a retro-inversal D amino acid peptide comprising RFHNPDKGSRGWENAAQDA (D-form; SEQ ID NO:3). These reverse peptides were derived from the forward human SAA 1.1 peptide ADQAANEWGRSGKDPNHFR (D-form; SEQ ID NO:11). Additional exemplary reverse peptides expected to enhance CEH activity based upon their similarity to SEQ ID NO:2 and SEQ ID NO:3 include, but are not limited to, reverse peptides comprising YKDPLGPPRYYNPDKGSRGHRNAEQDAITD (SEQ ID NO:4); YKDPLGPPRYYNPDKGSRGHRNAEQDA (SEQ ID NO:5); YKAPLGPPRYYNPDKGSRGHRNAEQDA (SEQ ID NO:6); YKEPLGAPRFHNPDKGSRGWENAAQDA (SEQ ID NO:7); RYYNPDKGSRGHRNAEQDA (SEQ ID NO:8); RFHNPDRGSRGWKNAAQDA (SEQ ID NO:9); or RFHNPDRGSRGWKNAAQD (SEQ ID NO:10) or portions thereof. Preferred reverse peptide variants include, but are not limited to, cyclic reverse peptides and retro-inversal D amino acid peptides comprising one or more D amino acids, which are at least equally effective and superior in some embodiments but less susceptible to degradation in vivo than corresponding L amino acid peptides. More preferred is a retro-inversal D amino acid peptide variant comprising all D amino acids.

The present invention also relates to mimetics of any of the above reverse peptides, reverse peptide variants or portions thereof.

Another aspect of the present invention relates to compositions with a formula of Y—Z or Q-Y—Z, wherein Y comprises a reverse peptide or mimetic thereof of the present invention with CEH enhancing activity; Z comprises a compound linked to Y that enhances the performance of Y; and in embodiments comprising Q, Q comprises another compound linked to Y—Z which enhances performance of the Q-Y—Z composition. Q may be identical to Z or different from Z. Exemplary Z or Q compounds include, but are not limited to a targeting agent, a second agent for treatment of atherosclerosis, cardiovascular disease or coronary heart disease, an agent which enhances solubility, absorption, distribution, half-life, bioavailability, stability, activity and/or efficacy, and an agent which reduces toxicity or side effects of the composition. Exemplary targeting agents of Z and/or Q include macrophage targeting agents such as, for example, a liposome, a microsphere, a ligand for a SAA receptor, hepatic targeting agents, antibodies and active fragments thereof such as, for example, Fab fragments, and additional agents specific to atherosclerotic plaques and/or inflammatory sites.

Another aspect of the present invention relates to pharmaceutical compositions comprising a reverse peptide, peptide variant, a mimetic thereof, or a Y—Z or Q-Y—Z composition which enhances CEH activity. Pharmaceutical compositions of the present invention further comprise a vehicle that is pharmaceutically suitable for in vivo administration. In one embodiment, the reverse peptide, mimetic thereof or the composition is complexed with a lipid. A phospholipid vesicle which encapsulates the reverse peptide, the mimetic thereof or the composition can also be used. In other embodiments, vehicles suitable for pharmaceutical administration in vivo may comprise aqueous solutions including, but not limited to, phosphate buffered saline or phosphate buffered saline containing glucose, preferably 0.01 to 10% weight/volume glucose, more preferably 5% weight/volume glucose.

Another aspect of the present invention relates to the use of these reverse peptides, mimetics thereof, compositions, or pharmaceutical compositions comprising these reverse peptides, mimetics thereof or compositions to modulate an activity of a cholesterol-metabolizing enzyme. In particular, the activity of CEH can be modulated using a reverse peptide, a mimetic thereof, a composition, or a pharmaceutical composition comprising a reverse peptide, a mimetic thereof, or a composition of the present invention. In a preferred embodiment of the present invention, the enzymatic activity is modulated in vivo. More preferred is modulation of the enzymatic activity in humans. Even more preferred is that the CEH activity be enhanced.

Another aspect of the present invention relates to use of these reverse peptides, mimetics thereof, compositions, or pharmaceutical compositions comprising these reverse peptides, mimetics thereof, or compositions to increase and/or promote the mobilization and efflux of stored cholesterol from macrophages and other cells located in atherosclerotic plaques. In a preferred embodiment of the present invention, the increase and/or promotion of the mobilization and efflux of stored cholesterol from macrophages and other cells located in atherosclerotic plaques occurs in vivo. More preferred is an increase and/or promotion of the mobilization and efflux of stored cholesterol from macrophages and other cells located in atherosclerotic plaques in humans. The reverse peptides, mimetics thereof, compositions and pharmaceutical compositions are also useful in modulating cholesterol metabolism in vivo in other cells including but not limited to hepatocytes, endothelial cells and epithelial cells.

Another aspect of the present invention relates to use of these reverse peptides, mimetics thereof, compositions or pharmaceutical compositions comprising these reverse peptides, mimetics thereof or compositions to increase and/or promote the mobilization and efflux of stored cholesterol from macrophages and other cells located at sites of inflammation. In a preferred embodiment of the present invention, the increase and/or promotion of the mobilization and efflux of stored cholesterol from macrophages and other cells located at sites of inflammation occurs in vivo. More preferred is an increase and/or promotion of the mobilization and efflux of stored cholesterol from macrophages and other cells located at sites of inflammation in humans.

Another aspect of the present invention relates to methods for treating and/or preventing atherosclerosis and/or regressing or decreasing formation of arterial atherosclerotic lesions in a subject comprising administering to the subject a reverse peptide, a mimetic thereof, a composition or a pharmaceutical composition of the present invention. In a preferred embodiment the subject is a human.

Another aspect of the present invention relates to methods for treatment of cardiovascular disease comprising administering to a subject a reverse peptide, a mimetic thereof, a composition or a pharmaceutical composition of the present invention. In a preferred embodiment the subject is a human.

Another aspect of the present invention relates to methods for treatment of coronary heart disease comprising administering to a subject a reverse peptide or a mimetic thereof, a composition or a pharmaceutical composition of the present invention. In a preferred embodiment the subject is a human.

Yet another aspect of the present invention relates to methods for treating and/or preventing or inhibiting inflammation in a subject comprising administering to the subject a reverse peptide or a mimetic thereof, a composition or a pharmaceutical composition of the present invention. In a preferred embodiment the subject is a human.

DETAILED DESCRIPTION OF THE INVENTION

Figure 1:
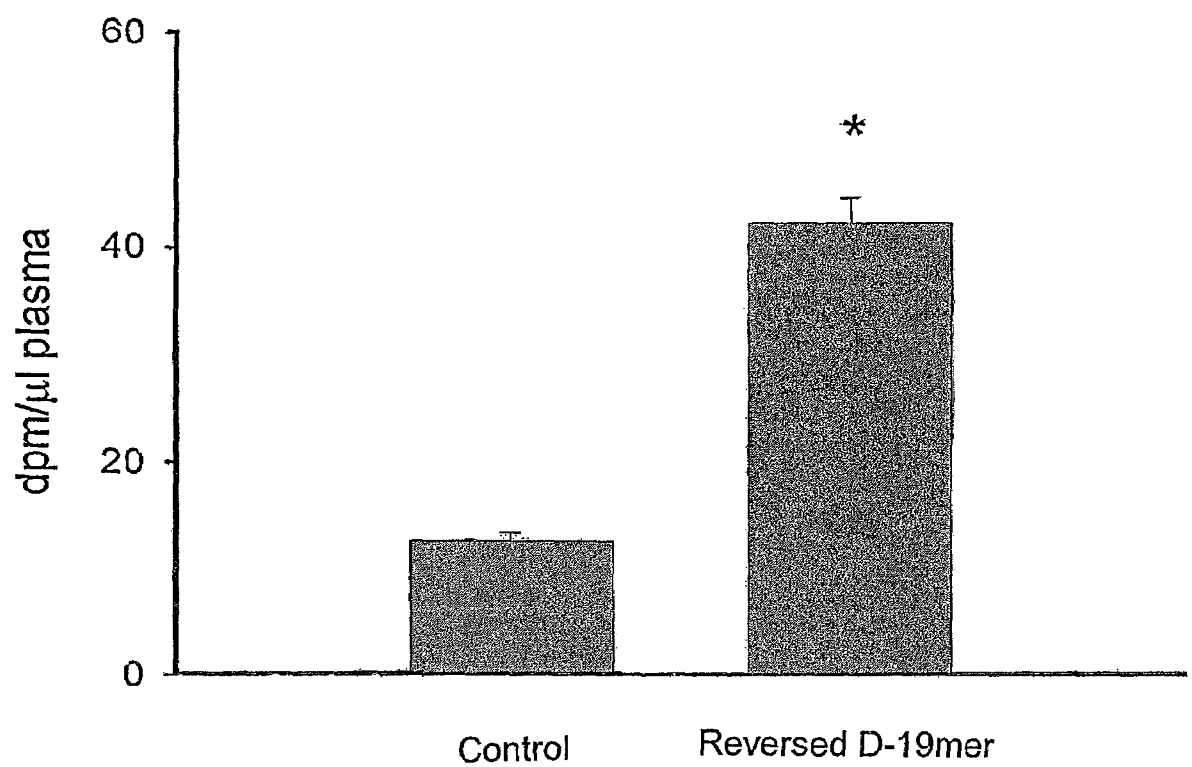
FIG. 1 is a bar graph comparing cholesterol efflux in an in vivo cholesterol export study in mice administered by tail vein injection retro-inversal D amino acid peptide RFHNPDKGSRGWENAAQDA (SEQ ID NO:3) at a total dose of 300 μg in 100 μl 0.9% saline versus control mice wherein vehicle (100 μl 0.9% saline) was administered by tail vein injection.

Approximately 13 million North Americans are taking cholesterol-lowering drugs, and the majority of these individuals are now treated with the category of drugs known as statins. Cholesterol synthesis inhibitors (statins) are for the most part considered safe and highly effective. However, there have been some recent setbacks for this drug class. For example, the 2001 voluntary recall of Bayer's statin Baycol™, the delayed North American introduction of AstraZeneca's statin Crestor™, and the recent concerns about the health risks associated with long-term statin use (Clearfield, M. B., (2002) *Expert Opin. Pharmacother.* 3:469-477) are indicative of the need for new drugs.

Thus, pharmaceutical companies are currently developing drugs that work via different mechanisms from that of the current marketed drugs. Treatment with two or more drugs that act through different mechanisms can, in fact, be additive or synergistic in their combined ability to reduce cholesterol levels (Brown, W. V. (2001) *Am. J. Cardiol.* 87(5A): 23B-27B; Buckert, E. (2002) *Cardiology* 97: 59-66). Ezetimibe (Zetia™, Merck), which was recently approved by the FDA, can significantly reduce cholesterol levels by itself. Furthermore, since ezetimibe works by decreasing cholesterol absorption (i.e. blocks cholesterol transport), it can also be given with cholesterol synthesis inhibitors (statins) to decrease plasma cholesterol levels to a greater extent than when either drug is given alone (Davis et al. (2001) *Arterioscler Thromb Vasc Biol.* 21: 2031-2038; Rader, D. J. (2002) *Am. J. Managed Care* 8 (2 Suppl): S40-44).

Other drugs such as avasimibe (Pfizer), eflucimibe (Eli Lilly) and pactimibe (Sankyo), which are or have been in clinical trials, are aimed at inhibiting acyl CoA:cholesterol acyl transferase (ACAT) activity.

Companies such as Esperion Therapeutics, a division of Pfizer, are developing ways to increase the levels of HDL, the so-called "good cholesterol", which plays a key role in the reverse cholesterol transport pathway, known to be important for the excretion of cholesterol out of the body.

Recent work conducted by scientists with, or associated with, Bruin Pharmaceuticals (Bruin) demonstrated that a short D amino acid peptide sequence within the ApoA-1 apolipoprotein, referred to as D-4F, can decrease plaque in apolipoprotein E-knockout mice (Navab et al. Circulation 2002 105:290-292; Navab et al. Circulation 2004 109:3215-3220). The D-4F peptide, which is 18 amino acids in length, has been shown to promote the reverse cholesterol transport (RCT) pathway and thus enhance cholesterol removal from atherosclerotic plaque (Navab et al. Circulation 2002 105: 290-292; Navab et al. Circulation 2004 109:3215-3220). This enhancement along the RCT pathway occurs at a step which is downstream from the macrophage ACAT and CEH steps. A retro-inversal D-4F peptide has been reported to have similar if not better activity as compared to D-4F in preventing plaque formation (Qin et al., Poster 619 presented at American Heart Association Meeting November 13-16, 2005 available at AHA with the extension scientific posters.com of the world wide web).

However, while there has been considerable effort by pharmaceutical companies to produce new compounds for treating atherosclerosis, there are currently no drugs on the market that have the ability to promote the mobilization and efflux of stored cholesterol from macrophages located in atherosclerotic plaques by enhancing CEH activity.

The accumulation of cholesterol in vascular cells such as macrophages is a defining pathological feature of atherosclerosis. Macrophages are key cells in the storage and removal of lipids. Their conversion to foam cells (cholesterol-laden macrophages) is an early and important pathological process in the formation of an atherosclerotic plaque. Macrophages and foam cells are used herein synonymously.

An enzyme critical for maintaining cellular cholesterol balance is cholesterol ester hydrolase (CEH), also referred to as cholesterol esterase and cholesteryl ester hydrolase. CEH promotes the removal or efflux of cholesterol from macrophages. This enzyme exists in an acidic as well as a neutral form and all aspects of the present invention are applicable to both forms, with modulation of the neutral form being preferred.

The in vitro effects of acute phase-HDL (AP-HDL; HDL-SAA) on CEH activities and on cellular cholesterol export have been studied using purified enzymes, cell homogenates, and whole cells. AP-HDL, as well as liposomes containing murine SAA2.1, have been shown to cause a marked enhancement of CEH activity in intact cholesterol-laden macrophages in tissue culture. In contrast, HDL alone, SAA2.1-free liposomes, and liposomes containing murine SAA1.1 or apoA-1 had no effect. Using macrophages preloaded with radio-labeled cholesterol and injected intravenously into either inflamed or un-inflamed mice, it was shown that the inflamed mice, which have high SAA2.1 levels, effluxed cholesterol more rapidly and to a greater extent (6-fold greater) than their un-inflamed counterparts. Further, using cholesterol-loaded macrophages pretreated with liposomes containing either murine SAA1.1, murine SAA2.1, or apoA-1 and then injected intravenously into un-inflamed mice, it has been shown that only liposomes containing murine isoform 2.1 recapitulated the major cholesterol releasing effect seen in inflamed mice. This work is described in detail in published PCT Application No. PCT/CA2004/000846, filed Jun. 11, 2004 and published U.S. Application No. US2004/0265982A1, filed Jun. 10, 2004, teachings of each of which are herein incorporated by reference in their entirety.

Using both in vitro and in vivo assays, the C-terminal 30-residue domain of murine SAA2.1 correlating to amino acids 74-103 of murine SAA2.1 was identified as the region of murine SAA2.1 that enhances CEH activity. In particular, the CEH activity-enhancing domain has been identified as correlating to amino acids 77-95 of murine SAA2.1. Further, isolated peptides with amino acid sequences comprising this domain or a portion thereof within murine SAA2.1, human SAA1.1 and human SAA2.1 have been shown to have a potent enhancing effect on macrophage CEH activity both in vitro and in vivo. These peptides, mimetics thereof, and compositions comprising these peptides or mimetics thereof are described in detail in published PCT Application No. PCT/CA2004/000846, filed Jun. 11, 2004 and published U.S. Application No. US2004/0265982A1, filed Jun. 10, 2004. Synthetic D amino acid peptides of this domain or portions thereof demonstrated to be equally effective and superior in some embodiments but less susceptible to degradation in vivo, are disclosed in U.S. patent application Ser. No. 11/268,690, filed Nov. 7, 2005, teachings of which are herein incorporated by reference in their entirety.

The inventor herein has now found that reverse peptides of this domain of mammalian serum amyloid A isoforms 2.1 (SAA2.1) and 1.1 (SAA1.1) or a portion thereof have a potent enhancing effect on macrophage CEH activity. Reverse peptides of this SAA CEH enhancing domain or a portion thereof shift macrophage cholesterol into a transportable form that is then rapidly exported from the cell in the presence of a cholesterol transporter, such as ABCA1 membrane transporter and a cholesterol acceptor, high density lipoprotein (HDL).

Table 1 and Table 2 set forth the current, as well as old (prior to 1999) nomenclature for SAA mouse and human proteins, respectively, as well as their corresponding forward amino acid sequences.

TABLE I

| Mouse SAA proteins | | | | | | | | | | | | | | | | | |
|---|---|---|---|---|---|---|---|---|---|---|---|---|---|---|---|---|---|
| New | Old | Seq ID# | −1 | 1 | 2 | 3 | 4 | 5 | 6 | 7 | 8 | 9 | 10 | 11 | 12 | 13 | 14 | 15 |
| SAA1.1 | SAA2 | 12 | | G | F | F | S | F | I | G | E | A | F | Q | G | A | G | D |
| SAA1.2 | SJL/J | 14 | | | | | | | | | | | | | | | | |
| SAA1.3 | mc1 | 15 | | | | | | | | S | | | | | | | | |
| SAA1.4 | mc2 | 16 | | | | | | | | S | | | | | | | | |
| SAA1.5 | mm1 | 17 | | | | | | | V | H | | | | | | | | |
| SAA1.6 | mm2 | 18 | | | | | | | | | | | | | | | | |
| SAA2.1 | SAA1 | 19 | | | | | | | V | H | | | | | | | | |
| SAA2.2 | CE/J | 20 | | | | | | | V | H | | | | L | | | | |
| SAA3 | | 21 | Q | R | W | V | Q | | M | K | | | G | | | S | R | |
| SAA4 | SAA5 | 22 | | D | | W | Y | | F | R | | | | | | T | W | |
| New | Old | Seq ID# | 16 | 17 | 18 | 19 | 20 | 21 | 22 | 23 | 24 | 25 | 26 | 27 | 28 | 29 | 30 | |
| SAA1.1 | SAA2 | 12 | M | W | R | A | Y | T | D | M | K | E | A | G | W | K | D | |
| SAA1.2 | SJL/J | 14 | | | | | | | | | | | | | | | | |
| SAA1.3 | mc1 | 15 | | | | | | | | | R | | | | | | | |
| SAA1.4 | mc2 | 16 | | | | | | | | | | | | | | | | |
| SAA1.5 | mm1 | 17 | | | | | | | | | | | | | | | | |
| SAA1.6 | mm2 | 18 | | | | | | | | | | | | | | | | |
| SAA2.1 | SAA1 | 19 | | | | | | | | | | | | N | | | N | |
| SAA2.2 | CE/J | 20 | | | | | | | | | | | | | | | | |
| SAA3 | | 21 | | | | | | S | | | | K | | | | | | |
| SAA4 | SAA5 | 22 | L | | | | | R | | N | L | | | N | Y | Q | N | |
| New | Old | Seq ID# | 31 | 32 | 33 | 34 | 35 | 36 | 37 | 38 | 39 | 40 | 41 | 42 | 43 | 44 | 45 | |
| SAA1.1 | SAA2 | 12 | G | D | K | Y | F | H | A | R | G | N | Y | D | A | A | Q | |
| SAA1.2 | SJL/J | 14 | | | | | | | | | | | | | | | | |
| SAA1.3 | mc1 | 15 | | | R | | | | | | | | | | | | | |
| SAA1.4 | mc2 | 16 | | | | | | | | | | | | | | | | |
| SAA1.5 | mm1 | 17 | | | | | | | | | | | | | | | | |
| SAA1.6 | mm2 | 18 | | | | | | | | | | | | | | | | |
| SAA2.1 | SAA1 | 19 | S | | | | | | | | | | | | | | | |
| SAA2.2 | CE/J | 20 | | | | | | | | | | | | | | | | |
| SAA3 | | 21 | S | | | | | | | | | | | | | | R | |
| SAA4 | SAA5 | 22 | A | | Q | | | Y | | | | | | E | | Q | | |
| New | Old | Seq ID# | 46 | 47 | 48 | 49 | 50 | 51 | 52 | 53 | 54 | 55 | 56 | 57 | 58 | 59 | 60 | |
| SAA1.1 | SAA2 | 12 | R | G | P | G | G | V | W | A | A | E | K | I | S | D | A | |
| SAA1.2 | SJL/J | 14 | | | | | | | | | | | | | | | | |
| SAA1.3 | mc1 | 15 | | | | | | | | | | | | | | | | |
| SAA1.4 | mc2 | 16 | | | | | | | | | | | | | | | | |
| SAA1.5 | mm1 | 17 | | | | | | | | | | | | | | | | |
| SAA1.6 | mm2 | 18 | | | | | | | | | | | | | | | | |
| SAA2.1 | SAA1 | 19 | | | | | | | | | | | | | | | G | |
| SAA2.2 | CE/J | 20 | | | | | | | | | | | | | | | | |
| SAA3 | | 21 | | | | | | A | | | | K | V | | | | | |
| SAA4 | SAA5 | 22 | | | S | | | I | | | | K | I | | | T | S | |
| New | Old | Seq ID# | 61 | 62 | 63 | 64 | 65 | 66 | 67 | 68 | 69 | 70 | 71 | 72 | 73 | 74 | 75 | |
| SAA1.1 | SAA2 | 12 | R | E | S | F | Q | E | F | F | G | R | G | H | E | D | T | |
| SAA1.2 | SJL/J | 14 | | | | | | | | | | | | | | | | |
| SAA1.3 | mc1 | 15 | | | | | | | | | | | | | | | | |
| SAA1.4 | mc2 | 16 | | | G | | | | | | | | | | | | | |
| SAA1.5 | mm1 | 17 | | | | | | | | | | | | | | | | |
| SAA1.6 | mm2 | 18 | | | | | | | | | | | | | | | | |
| SAA2.1 | SAA1 | 19 | | | A | | | | | | | | | | | | | |
| SAA2.2 | CE/J | 20 | | | A | | | | | | | | | | | | | |
| SAA3 | | 21 | | | | V | | K | | T | | H | | A | | | S | |
| SAA4 | SAA5 | 22 | | K | Y | | | G | L | L | N | H | | L | | T | L | |
| | | | | | | | | | | ↑ [NRYYFGIR] | | | | | | | | |
| New | Old | Seq ID# | 76 | 77 | 78 | 79 | 80 | 81 | 82 | 83 | 84 | 85 | 86 | 87 | 88 | 89 | 90 | |
| SAA1.1 | SAA2 | 12 | M | A | D | Q | E | A | N | R | H | G | R | S | G | K | D | |
| SAA1.2 | SJL/J | 14 | | | | | | | | | | | | | | | | |
| SAA1.3 | mc1 | 15 | | | | | | | | | | | | | | | | |
| SAA1.4 | mc2 | 16 | | | | | | | | | | | | | | | | |
| SAA1.5 | mm1 | 17 | | | | | | | | | | | | | | | | |
| SAA1.6 | mm2 | 18 | | | | | | | | | | | | | | | | |
| SAA2.1 | SAA1 | 19 | I | | | | | | | | | | | | | | | |

TABLE I-continued

Mouse SAA proteins

| | | | | | | | | | | | | | | | | | |
|---|---|---|---|---|---|---|---|---|---|---|---|---|---|---|---|---|---|
| SAA2.2 | CE/J | 20 | | | | | | | | | | | | | | | |
| SAA3 | | 21 | R | | | | F | | | E | W | | | | | | |
| SAA4 | SAA5 | 22 | Q | | T | | K | | E | E | W | | | | | | N |

| New | Old | Seq ID# | 91 | 92 | 93 | 94 | 95 | 96 | 97 | 98 | 99 | 100 | 101 | 102 | 103 |
|---|---|---|---|---|---|---|---|---|---|---|---|---|---|---|---|
| SAA1.1 | SAA2 | 12 | P | N | Y | Y | R | P | P | G | L | P | A | K | Y |
| SAA1.2 | SJL/J | 14 | | | | | | | | | | | D | | |
| SAA1.3 | mc1 | 15 | | | | | | | | | | | | | |
| SAA1.4 | mc2 | 16 | | | | | | | | | | | | | |
| SAA1.5 | mm1 | 17 | | | | | | | | | | | | | |
| SAA1.6 | mm2 | 18 | | | | | | | | | | | D | | |
| SAA2.1 | SAA1 | 19 | | | | | | | | | | | D | | |
| SAA2.2 | CE/J | 20 | | | | | | | | | | | D | | |
| SAA3 | | 21 | | | H | F | | | A | | | K | R | | |
| SAA4 | SAA5 | 22 | | | H | F | | | E | | | E | | F | |

TABLE II

Human SAA proteins

| New | Old | Seq ID# | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| SAA1.1 | SAA1α | 23 | R | S | F | F | S | F | L | G | E | A | F | D | G | A | R |
| SAA1.2 | SAA1β | 24 | | | | | | | | | | | | | | | |
| SAA1.3 | SAA1γ | 25 | | | | | | | | | | | | | | | |
| SAA1.4 | SAA1δ | 26 | | | | | | | | | | | | | | | |
| SAA1.5 | SAA1β | 27 | | | | | | | | | | | | | | | |
| SAA2.1 | SAA2α | 28 | | | | | | | | | | | | | | | |
| SAA2.2 | SAA2β | 29 | | | | | | | | | | | | | | | |
| SAA4 | | 30 | E | S | W | R | S | F | F | K | E | A | L | Q | G | V | G |
| New | Old | Seq ID# | 16 | 17 | 18 | 19 | 20 | 21 | 22 | 23 | 24 | 25 | 26 | 27 | 28 | 29 | 30 |
| SAA1.1 | SAA1α | 23 | D | M | W | R | A | Y | S | D | M | R | E | A | N | Y | I |
| SAA1.2 | SAA1β | 24 | | | | | | | | | | | | | | | |
| SAA1.3 | SAA1γ | 25 | | | | | | | | | | | | | | | |
| SAA1.4 | SAA1δ | 26 | | | | | | | | | | | | | | | |
| SAA1.5 | SAA1β | 27 | | | | | | | | | | | | | | | |
| SAA2.1 | SAA2α | 28 | | | | | | | | | | | | | | | |
| SAA2.2 | SAA2β | 29 | | | | | | | | | | | | | | | |
| SAA4 | | 30 | D | M | G | R | A | Y | M | D | I | M | I | S | M | H | Q |
| New | Old | Seq ID# | 31 | 32 | 33 | 34 | 35 | 36 | 37 | 38 | 39 | 40 | 41 | 42 | 43 | 44 | 45 |
| SAA1.1 | SAA1α | 23 | G | S | D | K | Y | F | H | A | R | G | N | Y | D | A | A |
| SAA1.2 | SAA1β | 24 | | | | | | | | | | | | | | | |
| SAA1.3 | SAA1γ | 25 | | | | | | | | | | | | | | | |
| SAA1.4 | SAA1δ | 26 | | | | | | | | | | | | | | | |
| SAA1.5 | SAA1β | 27 | | | | | | | | | | | | | | | |
| SAA2.1 | SAA2α | 28 | | | | | | | | | | | | | | | |
| SAA2.2 | SAA2β | 29 | | | | | | | | | | | | | | | |
| SAA4 | | 30 | N | S | N | R | Y | L | Y | A | R | G | N | Y | D | A | A |
| New | Old | Seq ID# | 46 | 47 | 48 | 49 | 50 | 51 | 52 | 53 | 54 | 55 | 56 | 57 | 58 | 59 | 60 |
| SAA1.1 | SAA1α | 23 | K | R | G | P | G | G | V | W | A | A | E | A | I | S | D |
| SAA1.2 | SAA1β | 24 | | | | | | | A | | | | | V | | | |
| SAA1.3 | SAA1γ | 25 | | | | | | | A | | | | | | | | |
| SAA1.4 | SAA1δ | 26 | | | | | | | A | | | | | V | | | N |
| SAA1.5 | SAA1β | 27 | | | | | | | A | | | | | V | | | |
| SAA2.1 | SAA2α | 28 | | | | | | | A | | | | | V | | | N |
| SAA2.2 | SAA2β | 29 | | | | | | | A | | | | | V | | | N |
| SAA4 | | 30 | Q | R | G | P | G | G | V | W | A | A | K | L | I | S | R |
| New | Old | Seq ID# | 61 | 62 | 63 | 64 | 65 | 66 | 67 | 68 | 69 | 70 | 71 | 72 | 73 | 74 | 75 |
| SAA1.1 | SAA1α | 23 | A | R | E | N | I | Q | R | F | F | G | H | G | A | E | D |
| SAA1.2 | SAA1β | 24 | | | | | | | | | | | | D | | | |
| SAA1.3 | SAA1γ | 25 | | | | | | | | | | | | | | | |
| SAA1.4 | SAA1δ | 26 | | | | | | | | | | | | | | | |
| SAA1.5 | SAA1β | 27 | | | | | | | | | | | | | | | |
| SAA2.1 | SAA2α | 28 | | | | | | | | L | T | | | | | | |
| SAA2.2 | SAA2β | 29 | | | | | | | | L | T | | R | | | | |

TABLE II-continued

| Human SAA proteins | | | | | | | | | | | | | | | | | |
|---|---|---|---|---|---|---|---|---|---|---|---|---|---|---|---|---|---|
| SAA4 | | 30 | S | R | V | Y | L | Q | G | L | I ↑ [DYYLFGNS] | S | T | V | L | E | D |
| New | Old | Seq ID# | 76 | 77 | 78 | 79 | 80 | 81 | 82 | 83 | 84 | 85 | 86 | 87 | 88 | 89 | 90 |
| SAA1.1 | SAA1α | 23 | S | L | A | D | Q | A | A | N | E | W | G | R | S | G | K |
| SAA1.2 | SAA1β | 24 | | | | | | | | | | | | | | | |
| SAA1.3 | SAA1γ | 25 | | | | | | | | | | | | | | | |
| SAA1.4 | SAA1δ | 26 | | | | | | | | | | | | | | | |
| SAA1.5 | SAA1β | 27 | | | | | | | | | | | | | | | |
| SAA2.1 | SAA2α | 28 | | | | | | | | | K | | | | | | R |
| SAA2.2 | SAA2β | 29 | | | | | | | | | K | | | | | | R |
| SAA4 | | 30 | S | K | S | N | E | K | A | E | E | W | G | R | S | G | K |

| New | Old | Seq ID# | 91 | 92 | 93 | 94 | 95 | 96 | 97 | 98 | 99 | 100 | 101 | 102 | 103 | 104 | |
|---|---|---|---|---|---|---|---|---|---|---|---|---|---|---|---|---|---|
| SAA1.1 | SAA1α | 23 | 23 | D | P | N | H | F | R | P | A | G | L | P | E | K | Y |
| SAA1.2 | SAA1β | 24 | | | | | | | | | | | | | | | |
| SAA1.3 | SAA1γ | 25 | | | | | | | | | | | | | | | |
| SAA1.4 | SAA1δ | 26 | | | | | | | | | | | | | | | |
| SAA1.5 | SAA1β | 27 | | | | | | | | | | | | | | | |
| SAA2.1 | SAA2α | 28 | | | | | | | | | | | | | | | |
| SAA2.2 | SAA2β | 29 | | | | | | | | | | | | | | | |
| SAA4 | | 30 | D | P | D | R | F | R | P | D | G | L | P | K | K | Y | |

These tables are based upon the disclosure in 1999 in Amyloid: Int. J. Exp. Clin. Invest. 6:67-70. The tables presented herein have been modified, however, to clarify alignment and provide numbering for residue (−1) of mouse isoform SAA3 comprising an additional amino acid.

By "reverse peptide" as used herein, it is meant a peptide having an amino acid sequence wherein the amino acids are positioned in opposite order to the forward amino acid sequence, or a portion thereof, depicted, for example, in Tables 1 and 2. Thus, for example, for full length murine SAA1.1 GFFSFIGEAFQGAGDMWRAYTD-MKEAGWKDGDKYFHARGNYDAAQRGPG-GVWAAEKISD ARESFQEFFGRGHEDTMADQEAN-RHGRSGKDPNYYRPPGLPAKY (SEQ ID NO:12), the reverse peptide is YKAPLGPPRYYNPDKGSRGHR-NAEQDAMTDEHGRGFFEQFSERAD-SIKEAAWVGGPGRQ AADYNGRAHFYKDGDKW-GAEKMDTYARWMDGAGQFAEGIFSFFG (SEQ ID NO:13). By reverse peptide it is meant to be inclusive of reverse L amino acid peptides, reverse D amino acid peptides, sometimes referred to as retro-inversal (also known as retro-inverso, retro-enantio, retro-all) D amino acid peptides, as well as peptides comprising L amino acids and D amino acids.

The ability of reverse peptides of the CEH enhancing domain of SAA or a portion thereof to enhance CEH activity was demonstrated in an in vivo mouse cholesterol export model. In these experiments, mice (n=4) were first injected intravenously with [$^3$H]cholesterol-laden macrophages and then injected 24 hours later with the exemplary retro-inversal D amino acid peptide RFHNPDKGSRGWENAAQDA (D-form; SEQ ID NO: 3). This peptide is the reverse sequence of the forward human D amino acid 19-mer peptide ADQAANEWGRSGKDPNHFR (D-form; SEQ ID NO:11) disclosed in U.S. patent application Ser. No. 11/268,690, filed Nov. 7, 2005, teachings of which are herein incorporated by reference in their entirety. The forward human D amino acid 19-mer peptide ADQAANEWGRSGKDPNHFR (D-form; SEQ ID NO:11) was demonstrated therein to be effective at increasing cholesterol efflux in vitro in both mouse and human cell culture experiments and in vivo in a subject upon intravenous and oral administration of an aqueous solution of the D amino acid containing forward peptide.

The retro-inversal D amino acid peptide RFHNPDKG-SRGWENAAQDA (SEQ ID NO: 3) at a total dose of 300 ug, was injected into the tail vein of each mouse that was previously (24 hours earlier) injected with $H^3$-radiolabeled cholesterol-loaded macrophages. This reverse peptide was dissolved in 0.9% saline and administered at a volume of 100 ul per mouse, to achieve a final total dose of 300 ug per mouse. Blood samples were collected 5 hours post reverse peptide injection. Approximately 25 μl of blood were collected from the tail vein of each animal. The blood samples were centrifuged to separate the red blood cells from the plasma and the [$^3$H]-cholesterol in plasma was determined by scintillation counting. Results are mean±SEM of four determinations.

As shown in FIG. 1 the retro-inversal D amino acid 19-mer RFHNPDKGSRGWENAAQDA (D-form; SEQ ID NO: 3) significantly enhanced in vivo macrophage cholesterol export over the vehicle control group (p=0.0004). This increase in macrophage cholesterol export was over 2.5-fold higher than control animals treated with saline vehicle alone. Saline vehicle does not enhance cholesterol export.

These data show that, similar to forward D amino acid peptides of the SAA CEH enhancing domain, retro-inversal D amino acid peptides of the present invention are capable of reaching distally-located cholesterol-loaded macrophages. Furthermore, these reverse peptides are capable of targeting and entering cholesterol-loaded macrophages and promoting macrophage cholesterol export. These effects are believed to be due, at least in part, to D amino acid peptides being in general resistant to enzymatic and non-enzymatic degradative processes.

The experiments set forth herein demonstrate that synthetic reverse peptides of the SAA CEH enhancing domain or a portion thereof, markedly increased in vivo cholesterol efflux. The data substantiate the utility of designing and using reverse peptides or mimetics thereof of the SAA CEH domain or a portion thereof to reduce or prevent atherogenesis and/or cause regression of an atherosclerotic plaque by increasing the efflux of cholesterol from macrophages located in an atherosclerotic lesion. Such reverse peptides or mimetics thereof will be useful in the treatment or prevention of atherosclerosis and in the treatment of coronary heart disease and cardiovascular disease associated with atherosclerosis.

Thus, the present invention provides reverse peptides, mimetics thereof, Y—Z and Q-Y—Z compositions, and pharmaceutical compositions comprising a reverse peptide, a mimetic thereof or a Y—Z or Q-Y—Z composition, for use in the prevention and/or treatment of atherosclerosis as well as coronary heart disease and cardiovascular disease associated with atherosclerosis and/or in the regression or decrease in formation of arterial atherosclerotic lesions. In a preferred embodiment, the reverse peptide or mimetic thereof is a retro-inversal D amino acid peptide or mimetics thereof of the present invention containing one or more D amino acids. Pharmaceutical compositions of the present invention comprise a reverse peptide of the SAA CEH enhancing domain of SAA2.1 or a portion thereof or a mimetic thereof, or a Y—Z or Q-Y—Z composition.

By "portion thereof" it is meant to be inclusive of reverse peptides exhibiting similar biological activities to the reverse peptides described herein but which, (1) comprise shorter fragments of the reverse sequence of the CEH enhancing domains of murine SAA2.1, murine SAA1.1, human SAA1.1 or human SAA2.1 described herein or (2) overlap with only part of the reverse sequence of the cholesterol enhancing domains of murine SAA2.1, murine SAA1.1, human SAA1.1 or human SAA2.1 described herein.

By "synthetic," as used herein it is meant that the peptide is prepared synthetically, either by chemical means or recombinantly.

Further, it will of course be understood, without the intention of being limited thereby, that a variety of substitutions of amino acids in the disclosed reverse peptides is possible while preserving the structure responsible for the CEH enhancing activity of the reverse peptides disclosed herein. Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could possibly be made, as could substitutions among the charged basic amino acids, lysine and arginine. Substitutions among the aromatic amino acids, including phenylalanine, histidine, tryptophan and tyrosine would also likely be possible. In some situations, histidine and basic amino acids lysine and arginine may be substituted for each other. These sorts of substitutions and interchanges are well known to those skilled in the art. Other substitutions might well be possible. It is expected that the greater the percentage of sequence identity of a variant peptide with a reverse peptide described herein, the greater the retention of biological activity. Accordingly, peptide variants having the activity of enhancing CEH as described herein are encompassed within the scope of this invention.

Preferred reverse peptides capable of enhancing CEH activity for use in the present invention comprise a synthetic peptide or a mimetic thereof comprising a formula $X_{18}X_{17}X_{16}X_{15}X_{14}X_{13}X_{12}X_{11}X_{10}X_9X_8X_7X_6X_5X_4X_3X_2X_1$ (SEQ ID NO:1) or a portion thereof wherein $X_1$ and $X_9$, $X_{12}$ or $X_{18}$ are amino acids capable of forming a salt bridge, $X_6$ is glutamic acid or lysine or an amino acid which is a conservative substitution thereof, and $X_2$, $X_3$, $X_4$, $X_5$, $X_7$, $X_8$, $X_{10}$, $X_{11}$, $X_{13}$, $X_{14}$, $X_{15}$, $X_{16}$, and $X_{17}$ are independently any amino acid. Preferred is a reverse peptide comprising $X_{18}X_{17}X_{16}X_{15}X_{14}X_{13}X_{12}X_{11}X_{10}X_9X_8X_7X_6X_5X_4X_3X_2X_1$ (SEQ ID NO:1) wherein $X_1$ and $X_9$, $X_{12}$ or $X_{18}$ are amino acids capable of forming a salt bridge, $X_2$ is glutamine or an amino acid which is a conservative substitution thereof, $X_3$ and $X_4$ are independently alanine or an amino acid which is a conservative substitution thereof, $X_5$ and $X_{15}$ are independently asparagine or an amino acid which is a conservative substitution thereof, $X_7$ is tryptophan or an amino acid which is a conservative substitution thereof, $X_8$ and $X_{11}$ are independently glycine or an amino acid which is a conservative substitution thereof, $X_{10}$ is serine or an amino acid which is a conservative substitution thereof, $X_{13}$ is aspartic acid or an amino acid which is a conservative substitution thereof, $X_{14}$ is proline or an amino acid which is a conservative substitution thereof, $X_{16}$ is histidine or an amino acid which is a conservative substitution thereof, and/or $X_{17}$ is phenylalanine or an amino acid which is a conservative substitution thereof. Examples of amino acid combinations capable of forming a salt bridge include $X_1$ being an aspartic acid and $X_9$, $X_{12}$ or $X_{18}$ being an arginine. It is preferred that the reverse peptide or mimetic thereof have equal to or less amino acid residues as compared to the full length forward SAA protein, more preferably less than 80 amino acid residues, more preferably less than 50 amino acids, more preferably less than 35, 30, or 25 amino acids and most preferably 20 or less, or 18 or less. As will be understood by the skilled artisan upon reading the disclosure, the minimal length of a reverse peptide of the present invention will be the lowest number of amino acids in sequence which maintain CEH enhancing properties while providing for cost effective production and/or minimizing degradation. In certain preferred embodiments, the reverse peptide or mimetic thereof comprises one or more D amino acids. Preferred is a reverse peptide comprising RFHNPDKGSRGWENAAQDA (SEQ ID NO:2) or a portion thereof. More preferred is a retro-inversal D amino acid peptide comprising RFHNPDKGSRGWENAAQDA (D-form; SEQ ID NO:3). Additional exemplary reverse peptides expected to enhance CEH activity based upon their similarity to SEQ ID NO:2 and SEQ ID NO:3 include, but are not limited to, reverse peptides comprising YKDPLGPPRYYNPDKGSRGHRNAEQDAITD(SEQ ID NO:4); YKDPLGPPRYYNPDKGSRGHRNAEQDA(SEQ ID NO:5); YKAPLGPPRYYNPDKGSRGHRNAEQDA (SEQ ID NO:6); YKEPLGAPRFHNPDKGSRGWENAAQDA (SEQ ID NO:7); RYYNPDKGSRGHRNAEQDA (SEQ ID NO:8); RFHNPDRGSRGWKNAAQDA (SEQ ID NO:9); or RFHNPDRGSRGWKNAAQD (SEQ ID NO:10) or portions thereof. In a preferred embodiment, the above exemplary peptides comprise one or more D amino acids.

Also preferred for use in the present invention to enhance CEH activity are compositions with a formula of Y—Z or Q-Y—Z. In these compositions Z is linked to Y and/or Q is linked to Y—Z via any acceptable binding means and selected based upon selection of Z or Q. Examples of acceptable binding means include, but are in no way limited to, covalent binding, noncovalent binding, hydrogen binding, antibody-antigen recognition, and ligand binding. In compositions with the formula Y—Z or Q-Y—Z, Y comprises a reverse peptide or mimetic thereof of the present invention with CEH enhancing activity; Z comprises a compound linked to Y that enhances the performance of Y; and in embodiments comprising Q, Q may be identical to Z or different from Z and also enhances performance of the composition Q-Y—Z. Preferred are compositions with retro-inversal D amino acid peptides or mimetics thereof containing one or more D amino acids. Exemplary Z or Q compounds include, but are not limited to, a targeting agent, a second agent for treatment of atherosclerosis, cardiovascular disease or coronary heart disease, an agent which enhances solubility, absorption, distribution, half-life, bioavailability, stability, activity and/or efficacy, and an agent which reduces toxicity or side effects of the composition. Exemplary targeting agents of Z and/or Q include macrophage targeting agents such as, for example, a liposome, a microsphere, a ligand for a SAA receptor, hepatic targeting agents, antibodies and active fragments thereof such as, for example, Fab fragments, and additional agents specific to atherosclerotic plaques and/or inflammatory sites.

By "human equivalent" as used herein, it is meant a reverse peptide sequence derived from human SAA2.1 or human SAA1.1 with similar activity to the murine peptides referenced herein.

By "mimetic" as used herein it is meant to be inclusive of reverse peptides, which may be recombinant, and peptidomimetics, as well as small organic molecules, which exhibit similar or enhanced CEH modulating activity. These include reverse peptide variants which comprise conservative amino acid substitutions relative to the reverse sequences of the native domains of SAA2.1 or SAA1.1 and reverse peptide variants which have a high percentage of sequence identity with the native domains of the reverse sequences of SAA2.1 or SAA1.1, at least, e.g., 70%, 75%, 80%, 85%, 90%, preferably at least 95%, 96%, 97%, 98%, or 99% sequence identity, and more preferably at least 99.5% or 99.9% sequence identity. Variant reverse peptides can be aligned with the reference reverse peptide sequence to assess percentage sequence identity in accordance with any of the well-known techniques for alignment. For example, a variant reverse peptide greater in length than a reference reverse peptide sequence is aligned with the reference reverse peptide sequence using any well known technique for alignment and percentage sequence identity is calculated over the length of the reference reverse peptide sequence, notwithstanding any additional amino acids of the variant reverse peptide, which may extend beyond the length of the reference reverse peptide sequence.

Preferred reverse variant peptides include, but are not limited to, retro-inversal D amino acid peptides comprising one or more D amino acids, which are also effective but generally less susceptible to degradation in vivo than corresponding L amino acid peptides, and cyclic peptides. As demonstrated herein, retro-inversal D amino acid peptides of the present invention are effective at increasing cholesterol efflux in vivo when administered intravenously in an aqueous vehicle. Like D forward peptides it is expected that the retro-inversal D amino acid peptides of the present invention will also be effective orally. Lipid/liposome formulations of reverse peptides of the present invention, like lipid/liposome formulations of the forward peptides of the present invention, are also expected to be effective at increasing cholesterol efflux. The reverse peptides and mimetics thereof are therefore believed to be effective at regressing and/or decreasing formation of arterial atherosclerotic lesions and treating or preventing atherosclerosis, cardiovascular disease, coronary heart disease and inflammation in a subject.

Cyclic peptides can be circularized by various means including but not limited to peptide bonds or depsicyclic terminal residues (i.e. a disulfide bond).

As used herein, the term "peptidomimetic" is intended to include analogs of peptides that serve as appropriate substitutes for the exemplary reverse peptides of SEQ ID NO:2 through 10 in modulating CEH activity. The peptidomimetic must possess not only similar chemical properties, e.g. affinity, to this peptide domain, but also efficacy and function. That is, a peptidomimetic exhibits function(s) of a CEH enhancing domain of SAA, without restriction of structure. Peptidomimetics of the present invention, i.e. analogs of the CEH enhancing domain of SAA2.1 or 1.1, include amino acid residues or other moieties which provide the functional characteristics described herein. Peptidomimetics and methods for their preparation and use are described in Morgan et al. 1989, "Approaches to the discovery of non-peptide ligands for peptide receptors and peptidases," In Annual Reports in Medicinal Chemistry (Vuirick, F. J. ed), Academic Press, San Diego, Calif., 243-253.

Mimetics of the present invention may be designed to have a similar structural shape to the CEH enhancing domain of SAA or a portion thereof. For example, mimetics according to the present invention of the CEH enhancing domain or a portion thereof may be designed to include a structure which mimics the salt bridge conformation of $X_{18}X_{17}X_{16}X_{15}X_{14}X_{13}X_{12}X_{11}X_{10}X_9X_8X_7X_6X_5X_4X_3X_2X_1$ (SEQ ID NO:1) or a portion thereof wherein $X_1$ and $X_9$, $X_{12}$ or $X_{18}$ are amino acids capable of forming a salt bridge, $X_6$ is glutamic acid or lysine or an amino acid which is a conservative substitution thereof, and $X_2$, $X_3$, $X_4$, $X_5$, $X_7$, $X_8$, $X_{10}$, $X_{11}$, $X_{13}$, $X_{14}$, $X_{15}$, $X_{16}$, and $X_{17}$ are independently any amino acid.

Mimetics of CEH enhancing domain of SAA or portion thereof can also be designed to have a similar structure to the synthetic reverse peptides of SEQ ID NO:2 through 10. These peptidomimetics may comprise peptide sequences with conservative amino acid substitutions as compared to SEQ ID NO:2 through 10 which interact with surrounding amino acids to form a similar structure to these synthetic reverse peptides. Conformationally restricted moieties such as a tetrahydroisoquinoline moiety may also be substituted for a phenylalanine, while histidine bioisoteres may be substituted for histidine to decrease first pass clearance by biliary excretion. Peptidomimetics of the present invention may also comprise peptide backbone modifications. Analogues containing amide bond surrogates are frequently used to study aspects of peptide structure and function including, but not limited to, rotational freedom in the backbone, intra- and intermolecular hydrogen bond patterns, modifications to local and total polarity and hydrophobicity, and oral bioavailability. Examples of isosteric amide bond mimics include, but are not limited to, $\psi[CH_2S]$, $\psi[CH_2NH]$, $\psi[CSNH_2]$, $\psi[NHCO]$, $\psi[COCH_2]$ and $\psi[(E)$ or $(Z)CH{=}CH]$.

Mimetics can also be designed with extended and/or additional amino acid residue repeats as compared to the reverse sequence of the naturally occurring CEH enhancing domain of SAA or portion thereof.

Identification of these reverse peptides also permits molecular modeling based on these reverse peptides for design, and subsequent synthesis, of small organic molecules that have CEH enhancing activities. These small organic molecules mimic the structure and activity of the reverse peptides of SEQ ID NO: 1 through 10. However, instead of comprising amino acids, these small organic molecules comprise bioisosteres thereof, substituents or groups that have chemical or physical similarities, and exhibit broadly similar biological activities.

Bioisosterism is a lead modification approach used by those skilled in the art of drug design and shown to be useful in attenuating toxicity and modifying activity of a lead compound such as SEQ ID NO:1, 2, 3, 4, 5, 6, 7, 8, 9, or 10. Bioisosteric approaches are discussed in detail in standard reference texts such as The Organic Chemistry of Drug Design and Drug Action (Silverman, R B, Academic Press, Inc. 1992 San Diego, Calif., pages 19-23). Classical bioisosteres comprise chemical groups with the same number of valence electrons but which may have a different number of atoms. Thus, for example, classical bioisosteres with univalent atoms and groups include, but are not limited to: $CH_3$, $NH_2$, OH, F and Cl; Cl, $PH_2$ and SH; Br and i-Pr; and I and t-Bu. Classical bioisosteres with bivalent atoms and groups include, but are not limited to: —$CH_2$— and NH; O, S, and Se; and $COCH_2$, CONHR, $CO_2R$ and COSR. Classical bioisosteres with trivalent atoms and groups include, but are not limited to: CH═ and N═; and P═ and As═. Classical bioisosteres with tetravalent atoms include, but are not limited to: C and Si; and ═$C^+$═, ═$N^+$═ and ═$P^+$═. Classical bioisosteres with ring equivalents include, but are not limited to: benzene and thiophene; benzene and pyridine; and tetrahydrofuran, tetrahydrothiophene, cyclopentane and pyrrolidine. Nonclassical bioisosteres still produce a similar biological activity, but do not have the same number of atoms and do not fit the electronic and steric rules of classical isosteres. Exemplary nonclassical bioisoteres are shown in the following Table.

| Nonclassical Biosteres |
| --- |
| 1. Carbonyl group |
| 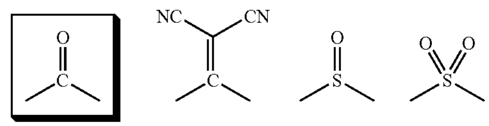 |
| 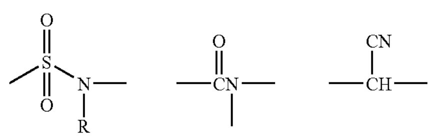 |
| 2. Carboxylic acid group |
| 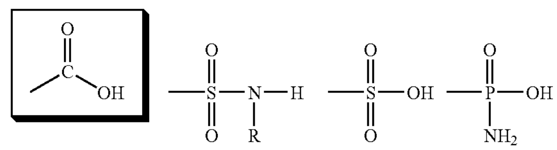 |
| 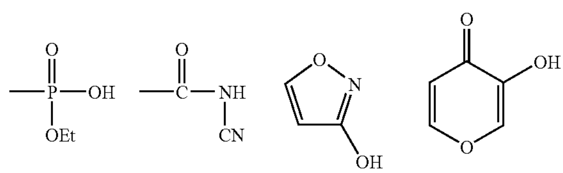 |
| 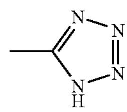 |
| 3. Hydroxy group |
| 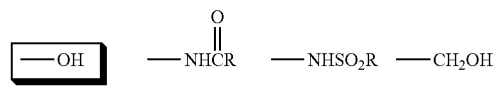  |
| 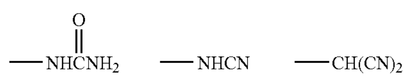  |
| 4. Catachol |
| 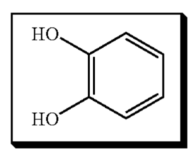 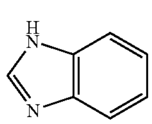 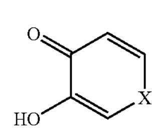 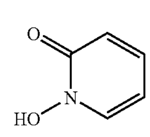 |
| X = O, NR |

-continued

Nonclassical Biosteres

5. Halogen

X $CF_3$ CN $N(CN)_2$ $C(CN)_3$

6. Thioether

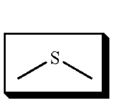

O

NC CN

CN
N

7. Thiourea

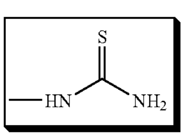

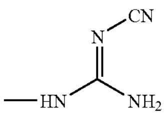

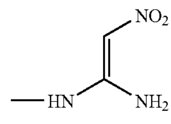

8. Azomethine

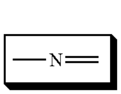

CN
C

9. Pyridine

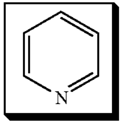

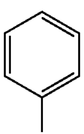

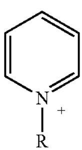

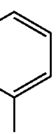

10 Spacer group

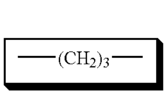

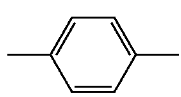

11. Hydrogen

H F

Additional bioisosteric interchanges useful in the design of small organic molecule mimetics of the present invention include ring-chain transformations.

A reverse peptide, a mimetic thereof or a Y—Z or Q-Y—Z composition of the present invention is preferably formulated with a vehicle pharmaceutically acceptable for administration to a subject, preferably a human, in need thereof. Methods of formulation for such compositions are well known in the art and taught in standard reference texts such as *Remington's Pharmaceutical Sciences*, Mack Publishing Co., Easton, Pa., 1985. A composition of the present invention may comprise a single reverse peptide, a mimetic thereof or a Y—Z or Q-Y—Z composition which modulates CEH activity.

By the terms "modulate" modulation" and/or "modulating" as used herein with respect to CEH activity it is meant an enhancing or increase in CEH activity.

Compositions of the present invention may be administered alone or in combination with a second cholesterol-lowering drug or agent. For example, a composition of the present invention comprising a reverse peptide of SEQ ID NO:1, 2, 3, 4, 5, 6, 7, 8, 9, or 10 or a mimetic thereof which inhibits CEH activity, can be administered to a subject in combination with an ACAT inhibitor. Exemplary ACAT inhibitors include but are not limited to avasimibe (Pfizer), eflucimibe (Eli Lilly) and pactimibe (Sankyo). Compositions of the present invention may also be administered to a subject with an apolipoprotein free cholesterol acceptor (Rothblat et al. J. Lipid Res. 1999 40:781-796; Li et al. Biochimica Biophysica Acta 1995 1259:227-234; Jian et al. J. Biol. Chem. 1998 273(10):5599-5606). An example of an apolipoprotein free cholesterol acceptor is cyclodextrin. Additional exemplary cholesterol-lowering drugs or agents which can be administered in combination with a reverse peptide, mimetic thereof or composition of the present invention include, but are not limited to, statins, resins, bile acid sequestrants (Bays et al. Expert Opinion on Pharmacotherapy 2003 4(11):1901-38; Kajinami et al. Expert Opinion on Investigational Drugs 2001 11(6):831-5), niacin (Van et al. Am. J. Cardiol. 2002 89(11):1306-8; Ganji et al. J. Nutri. Biochem. 2003 14(6): 298-305; Robinson et al. Progress in Cardiovasc. Nursing 2001 16(1):14-20; Knopp, R. H. Am. J. Cardiol. 2000 86(12A):51L-56L), liver X receptor agonists (Tontonoz et al. Molecular Endocrinology 2003 17:985-993), calcium (Ca2+) antagonists (Delsing et al. Cardiovasc. Pharmacol. 2003 42(1):63-70) and modulators of peroxisome proliferator-activated receptors (PPARs; Lee et al. Endocrinology 2003 144:2201-2207).

A preferred formulation for use in the present invention is complexing the reverse peptide, mimetic thereof or Y—Z or Q-Y—Z composition with a lipid. Also preferred as a formulation is encapsulation of the reverse peptide, mimetic thereof or Y—Z or Q-Y—Z composition in a phospholipid vesicle. An exemplary phospholipid vesicle useful in the present invention is a liposome. Liposomes containing the reverse peptide, mimetic thereof or Y—Z or Q-Y—Z composition of the present invention can be prepared in accordance with any of the well known methods such as described by Epstein et al. (Proc. Natl. Acad. Sci. USA 82: 3688-3692 (1985)), Hwang et al. (Proc. Natl. Acad. Sci. USA 77: 4030-4034 (1980)), EP 52,322, EP 36,676; EP 88,046; EP 143,949; EP 142,641; Japanese Pat. Appl. 83-118008, and EP 102,324, as well as U.S. Pat. Nos. 4,485,045 and 4,544,545, the contents of which are hereby incorporated by reference in their entirety. Preferred liposomes are of the small (about 200-800 Angstroms) unilamellar type in which the lipid content is greater than about 10 mol. percent cholesterol, preferably in a range of 10 to 40 mol. percent cholesterol, the selected proportion being adjusted for optimal peptide therapy. However, as will be understood by those of skill in the art upon reading this disclosure, phospholipid vesicles other than liposomes can also be used.

As demonstrated herein, another preferred formulation contains a reverse peptide, more preferably a retro-inversal D amino acid peptide comprising one or more D amino acids and an aqueous vehicle suitable for intravenous or oral administration.

Formulations expected to be useful in the present invention, e.g., intravenous formulations, include, but are not limited to, sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and oils (e.g., vegetable oil). The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the reverse peptide of the present invention in the required amount in an appropriate solvent with one or a combination of ingredients enumerated above, as required, followed by filter sterilization. Generally, dispersions are prepared by incorporating the reverse peptide of the present invention into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the peptide) optionally plus any additional desired ingredient from a previously sterile-filtered solution thereof.

Solid dosage forms for oral administration of a reverse peptide of the present invention include, but are not limited to, ingestible capsules, tablets, pills, lollipops, powders, granules, elixirs, suspensions, syrups, wafers, sublingual or buccal tablets, troches, and the like. In such solid dosage forms the reverse peptide is mixed with at least one inert, pharmaceutically acceptable excipient or diluent or assimilable edible carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the reverse peptide in the compositions and preparations may, of course, be varied. The amount of the reverse peptide in such therapeutically useful compositions is such that a suitable dosage will be obtained.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The reverse peptides can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the reverse peptide, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the reverse peptide, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The reverse peptides, mimetics thereof, compositions or pharmaceutical compositions of the present invention can also be administered via a coronary stent implanted into a patient. Coronary stents which elute a reverse peptide, a mimetic thereof, a composition or a pharmaceutical composition of the present invention can be prepared and implanted in accordance with well known techniques (See, for example, Woods et al. (2004) Annu. Rev. Med. 55:169-78); al-Lamce et al. (2003) Med. Device Technol. 2003 14:12-141 Lewis et al. 2002 J. Long Term Eff. Med. Implants 12:231-50; Tsuji et al. 2003 Int. J. Cardiovasc. Intervent. 5:13-6).

Pharmaceutical compositions of the present invention are useful in modulating the activity of a cholesterol-metabolizing enzyme, and in particular, the activity of CEH. In a preferred embodiment, the pharmaceutical compositions are used to modulate enzymatic activity in macrophages. More preferably, the pharmaceutical compositions are used to modulate enzymatic activity in vivo. More preferably, the pharmaceutical compositions are used to modulate enzymatic activity in mammals and in particular humans. More preferably, the pharmaceutical compositions are used to enhance CEH activity in mammals and in particular humans.

Pharmaceutical compositions of the present invention are also useful in promoting the mobilization and efflux of stored cholesterol located in atherosclerotic plaques and/or sites of inflammation. In a preferred embodiment, the pharmaceutical compositions are used to promote the mobilization and efflux of stored cholesterol from macrophages and other cells (e.g. hepatocytes, smooth muscle cells, endothelial cells and epithelial cells), including cells and tissues located in atherosclerotic plaques or sites of inflammation in vivo. More preferably, the pharmaceutical compositions are used to promoting the mobilization and efflux of stored cholesterol from macrophages and other cells and tissues located in atherosclerotic plaques or sites of inflammation in mammals and in particular humans.

Accordingly, the compositions of the present invention can be administered to a subject, preferably a mammal, more preferably a human, to treat and/or prevent atherosclerosis. The compositions may be administered by various routes including, but not limited to, orally, intravenously, intramuscularly, intraperitoneally, topically, subcutaneously, rectally, dermally, sublingually, buccally, intranasally or via inhalation. In a preferred embodiment, the composition administered comprises a retro-inversal D amino acid peptide or mimetic thereof with one or more D amino acids. The formulation and route of administration as well as the dose and frequency of administration can be selected routinely by those skilled in the art based upon the severity of the condition being treated, as well as patient-specific factors such as age, weight and the like. The prolonged activity of forward peptides of this domain in promoting cholesterol efflux from macrophages is indicative of the feasibility of daily, every other day or semi-weekly dosing regime for the pharmaceutical compositions comprising a reverse peptide, mimetic thereof, or composition of the present invention as well.

In addition to the above-described in vitro and in vivo assays, efficacy of reverse peptides, mimetics thereof and compositions of the present invention to treat and/or prevent atherosclerosis can also be demonstrated in an animal model such as the apoE knockout mouse model of atherogenesis (Davis et al. Arterioscler Thromb Vasc Biol. 2001 21:2031-2038). These mice, when placed on an atherogenic diet (as described by Tam et al. J. Lipid Res. 2005 46:2091-2101), rapidly deposit lipid into their aortas. The apoE knockout mice are a validated model of atherosclerosis and were used to demonstrate the effectiveness of ezetimibe (Zetia™; Merck) in reducing atherosclerosis (Davis et al. Arterioscler Thromb Vasc Biol. 2001 21:2031-2038). The efficacy of reverse peptides, mimetics thereof and compositions of the present invention, such as, e.g., those comprising one or more reverse peptides of SEQ ID NO: 1, 2, 3, 4, 5, 6, 7, 8, 9, or 10 or a mimetic thereof, in treating or preventing atherosclerosis can be demonstrated in similar fashion.

The in vivo effectiveness of a reverse peptide, mimetic thereof or composition of the present invention, such as one comprising a reverse peptide of SEQ ID NO:1, 2, 3, 4, 5, 6, 7, 8, 9 or 10 in preventing or reducing the degree of atherosclerosis, can be demonstrated in the above rodent model for atherogenesis. To demonstrate the ability to cause progression of atherosclerosis, then regression of atherosclerosis in animals treated with a reverse peptide, mimetic thereof or composition of the present invention, the rodent is first placed on an atherogenic diet for two weeks. The animals are then divided into three groups. The first group of animals serves as the baseline group. These animals are sacrificed just prior to treatment of the second and third groups of animals and the aortas are analyzed as described below. The second group of animals continues on the diet for an additional two weeks and is treated with vehicle only. The third group of animals continues on the diet for the same period but also receives a reverse peptide, mimetic thereof or composition of the present invention. The effects of a reverse peptide, mimetic thereof or composition of the present invention on aortic atherosclerosis are assessed at the termination of the experiment, when the aorta is removed from the animals and opened longitudinally. The area of the endothelial surface occupied by lipid is measured. Histological sections of aorta are also prepared for microscopic analysis and total lipids are isolated to measure the quantity of cholesterol per wet weight of tissue.

Administration of pharmaceutical compositions of the present invention is also expected to be useful in the treatment of coronary heart disease and cardiovascular disease and in the prevention or treatment of inflammation.

The invention is further illustrated by the following examples, which should not be construed as further limiting. The contents of all references, pending patent applications, and published patents cited throughout this application are hereby expressly incorporated by reference.

EXAMPLES

Example 1

Animals

Swiss-white CD1 6-8 week old female mice were obtained from Charles River, Montreal, Quebec. Mice were kept in a temperature controlled room on a 12 hour light/dark cycle. They were fed with Purina Lab Chow pellets and water ad libitum.

Example 2

Chemicals

All chemicals were reagent grade and purchased from Fisher Scientific (Nepean, Ont.), Sigma (St. Louis, Mo.), ICN (Aurora, Ohio), or BioRad (Hercules, Calif.). Dulbecco's Modified Eagle's Medium (DMEM) and fetal bovine serum (FBS) were purchased from Life Technologies (Burlington, Ont.). Radiolabeled [1,2,6,7-$^3$H(N)]-cholesterol (82 Ci/mmol) was obtained from DuPont NEN (Boston, Mass.).

Example 3

Reverse Peptides

Peptides were synthesized by solid-phase chemistry using a PE Applied Biosystems 433A peptide synthesizer. The purity of the synthetic peptides was established by analytical high-performance liquid chromatography (HPLC) and ion spray mass spectrometry. The peptides were dialyzed against distilled water and lyophilized before use.

Example 4

Increase in Cholesterol Efflux In Vivo with Reverse Peptide

J774 cells cultured in 6-well plates were enriched with cholesterol by incubating with red blood cell (RBC) membrane fragments (175 μg as cholesterol) that had been previously labeled with 0.5 μCi/ml [$^3$H]-cholesterol at 37° C. for 24 hours in 0.2% bovine serum albumin (BSA). After loading with the labelled RBC membrane for 6 hours, cells were then washed with phosphate-buffered saline/BSA (PBS/BSA) three times followed by an 18 hour equilibration period during which monolayers were exposed to DMEM/BSA (see Kisilevsky and Tam, J. Lipid Res. 2003 44:2257-2269).

Cells were washed four times with PBS/BSA and then detached from the culture dishes. Two hundred thousand cells in 100 μl PBS were injected into each mouse (n=4) through the tail vein. Twenty-four hours post cell injection, approximately 25 μl of blood was collected from the tail vein of each animal into heparinized capillary tubes. These tubes were then centrifuged for 5 minutes in an Adams Autocrit Centrifuge to separate red blood cells from plasma. Baseline cholesterol efflux was determined by measuring the amount of [$^3$H]-cholesterol in plasma by scintillation spectrometry.

To study whether export of cholesterol from J774 cells to plasma is modulated by the retro-inversal peptide RFHNPDKGSRGWENAAQDA (D-form; SEQ ID NO:3), 24 hours after injection of [$^3$H]-cholesterol-loaded J774 macrophages into mice and after the first blood sample was collected, the same animals received non-liposome formulated retro-inversal peptide RFHNPDKGSRGWENAAQDA (D-form; SEQ ID NO:3) at a total dose of 300 μg dissolved in 100 μl of PBS. The peptide was injected into the tail vein of each animal.

Five hours following intravenous injection of the reverse peptide, approximately 25 μl of blood were collected from the tail vein of each animal into heparinized capillary tubes and cholesterol efflux was determined as described above.

Data from this study are set forth in FIG. 1.

Example 5

Statistical Analysis

Unpaired Student's t tests were used to compare group means. A value of P<0.05 was considered statistically significant.

What is claimed is:

1. A reverse peptide relative to a forward amino acid sequence of a cholesterol ester hydrolase enhancing domain of a mammalian serum amyloid A protein, which reverse peptide enhances cholesterol ester hydrolase activity, said reverse peptide having at least 70% sequence identity with RFHNPDKGSRGWENAAQDA (D-form; SEQ ID NO:3), sequence identity being calculated over the length of SEQ ID NO:3, notwithstanding any additional amino acids of said reverse peptide which may extend beyond the length of SEQ ID NO:3, wherein said reverse peptide has less than 80 amino acid residues.

2. The reverse peptide of claim 1 which has 18 to 79 amino acid residues.

3. The reverse peptide of claim 1 comprising the retroinversal peptide RFHNPDKGSRGWENAAQDA (D-form; SEQ ID NO:3).

4. The reverse peptide of claim 1 which has at least 80% sequence identity with RFHNPDKGSRGWENAAQDA (D-form; SEQ ID NO:3).

5. The reverse peptide of claim 1 which has at least 90% sequence identity with RFHNPDKGSRGWENAAQDA (D-form; SEQ ID NO:3).

6. The reverse peptide of claim 1 which has at least 95% sequence identity with RFHNPDKGSRGWENAAQDA (D-form; SEQ ID NO:3).

7. The reverse peptide of claim 1 which has one or more conservative amino acid substitutions in the amino acid sequence of the peptide comprising RFHNPDKGSRG-WENAAQDA (D-form; SEQ ID NO:3).

8. A composition having a formula:

Y—Z wherein Y comprises the reverse peptide of claim 1; and wherein Z comprises a compound linked to Y that enhances the performance of Y.

9. The composition of claim 8 wherein Z comprises a targeting agent, a second agent for treatment of atherosclerosis, cardiovascular disease or coronary heart disease, an agent which enhances solubility, absorption, distribution, half-life, bioavailability, stability, activity and/or efficacy, or an agent which reduces toxicity or side effects of Y.

10. The composition of claim 8 further comprising Q linked to Y—Z wherein Q is identical to Z or different from Z and wherein Q comprises a targeting agent, a second agent for treatment of atherosclerosis, cardiovascular disease or coronary heart disease, an agent which enhances solubility, absorption, distribution, half-life, bioavailability, stability, activity and/or efficacy, or an agent which reduces toxicity or side effects of Y.

11. A pharmaceutical composition comprising the reverse peptide of claim 1 or a composition having a formula:

Y—Z wherein Y comprises the reverse peptide of claim 1; and wherein Z comprises a compound linked to Y that enhances the performance of Y;

and a pharmaceutically acceptable vehicle.

12. The pharmaceutical composition of claim 11 further comprising a second agent for treatment of atherosclerosis, cardiovascular disease or coronary heart disease.

13. The pharmaceutical composition of claim 11 wherein the pharmaceutically acceptable vehicle is suitable for oral, intravenous, intramuscular, intraperitoneal, topical, subcutaneous, rectal, dermal, sublingual, buccal, intranasal or inhalation administration.

14. The pharmaceutical composition of claim 11 wherein the reverse peptide or the composition is complexed with a lipid.

15. The pharmaceutical composition of claim 11 wherein the reverse peptide or the composition is enclosed in a phospholipid vesicle.

16. A method for enhancing activity of cholesterol ester hydrolase in a subject comprising administering to the subject the pharmaceutical composition of claim 11.

17. The method of claim 16 wherein the cholesterol ester hydrolase is in a macrophage.

18. The method of claim 16 further comprising administering a second agent for treatment of atherosclerosis, cardiovascular disease or coronary heart disease.

19. The method of claim 18 wherein the second agent is an acyl CoA:cholesterol acyl transferase inhibitor, an apolipoprotein free cholesterol acceptor, a statin, a resin, a bile acid sequestrant, niacin, a liver X receptor agonist, a calcium antagonist or a modulator of peroxisome proliferator-activated receptors.

20. The method of claim 18 wherein the cholesterol ester hydrolase is in a macrophage.

21. A method for treating atherosclerosis or regressing or decreasing formation of arterial atherosclerotic lesions in a subject comprising administering to the subject the pharmaceutical composition of claim 11.

22. The method of claim 21 further comprising administering a second agent for treatment of atherosclerosis, cardiovascular disease or coronary heart disease.

23. The method of claim 22 wherein the second agent is an acyl CoA:cholesterol acyl transferase inhibitor, an apolipoprotein free cholesterol acceptor, a statin, a resin, a bile acid sequestrant, niacin, a liver X receptor agonist, a calcium antagonist or a modulator of peroxisome proliferator-activated receptors.

24. A method for treating coronary heart disease or cardiovascular disease in a subject comprising administering to the subject the pharmaceutical composition of claim 11.

25. The method of claim 24 further comprising administering a second agent for treatment of atherosclerosis, cardiovascular disease or coronary heart disease.

26. The method of claim 25 wherein the second agent is an acyl CoA:cholesterol acyl transferase inhibitor, an apolipoprotein free cholesterol acceptor, a statin, a resin, a bile acid sequestrant, niacin, a liver X receptor agonist, a calcium antagonist or a modulator of peroxisome proliferator-activated receptors.

27. A method for preventing or inhibiting inflammation in a subject comprising administering to the subject the pharmaceutical composition of claim 11.

* * * * *

SEQUENCE LISTING

```
<160> NUMBER OF SEQ ID NOS: 30

<210> SEQ ID NO 1
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X=amino acid capable for forming salt bridge
<220> FEATURE:
<221> NAME/KEY: MISC_FEATURE
<222> LOCATION: (2)..(2)
<223> OTHER INFORMATION: X=any amino acid
<220> FEATURE:
<221> NAME/KEY: MISC_FEATURE
<222> LOCATION: (3)..(3)
<223> OTHER INFORMATION: X=any amino acid
<220> FEATURE:
<221> NAME/KEY: MISC_FEATURE
<222> LOCATION: (4)..(4)
<223> OTHER INFORMATION: X=any amino acid
<220> FEATURE:
<221> NAME/KEY: MISC_FEATURE
<222> LOCATION: (5)..(5)
<223> OTHER INFORMATION: X=any amino acid
<220> FEATURE:
```

-continued

```
<221> NAME/KEY: MISC_FEATURE
<222> LOCATION: (6)..(6)
<223> OTHER INFORMATION: X=any amino acid
<220> FEATURE:
<221> NAME/KEY: MISC_FEATURE
<222> LOCATION: (7)..(7)
<223> OTHER INFORMATION: X=amino acid capable of forming salt bridge
<220> FEATURE:
<221> NAME/KEY: MISC_FEATURE
<222> LOCATION: (8)..(8)
<223> OTHER INFORMATION: X=any amino acid
<220> FEATURE:
<221> NAME/KEY: MISC_FEATURE
<222> LOCATION: (9)..(9)
<223> OTHER INFORMATION: X=any amino acid
<220> FEATURE:
<221> NAME/KEY: MISC_FEATURE
<222> LOCATION: (10)..(10)
<223> OTHER INFORMATION: X=amino acid capable of forming salt bridge
<220> FEATURE:
<221> NAME/KEY: MISC_FEATURE
<222> LOCATION: (11)..(11)
<223> OTHER INFORMATION: X=any amino acid
<220> FEATURE:
<221> NAME/KEY: MISC_FEATURE
<222> LOCATION: (12)..(12)
<223> OTHER INFORMATION: X=any amino acid
<220> FEATURE:
<221> NAME/KEY: MISC_FEATURE
<222> LOCATION: (13)..(13)
<223> OTHER INFORMATION: X= glutamic acid or lysine or conservative
      substitution thereof
<220> FEATURE:
<221> NAME/KEY: MISC_FEATURE
<222> LOCATION: (14)..(14)
<223> OTHER INFORMATION: X= any amino acid
<220> FEATURE:
<221> NAME/KEY: MISC_FEATURE
<222> LOCATION: (15)..(15)
<223> OTHER INFORMATION: X= any amino acid
<220> FEATURE:
<221> NAME/KEY: MISC_FEATURE
<222> LOCATION: (16)..(16)
<223> OTHER INFORMATION: X= any amino acid
<220> FEATURE:
<221> NAME/KEY: MISC_FEATURE
<222> LOCATION: (17)..(17)
<223> OTHER INFORMATION: X= any amino acid
<220> FEATURE:
<221> NAME/KEY: MISC_FEATURE
<222> LOCATION: (18)..(18)
<223> OTHER INFORMATION: X= amino acid capable of forming salt bridge

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa


<210> SEQ ID NO 2
<211> LENGTH: 19
<212> TYPE: PRT
<213> ORGANISM: Artificial sequence
<220> FEATURE:
<223> OTHER INFORMATION: Synthetic

<400> SEQUENCE: 2

Arg Phe His Asn Pro Asp Lys Gly Ser Arg Gly Trp Glu Asn Ala Ala
1               5                   10                  15

Gln Asp Ala


<210> SEQ ID NO 3
<211> LENGTH: 19
<212> TYPE: PRT
```

-continued

<213> ORGANISM: Artificial sequence
<220> FEATURE:
<223> OTHER INFORMATION: Synthetic

<400> SEQUENCE: 3

```
Arg Phe His Asn Pro Asp Lys Gly Ser Arg Gly Trp Glu Asn Ala Ala
1               5                   10                  15

Gln Asp Ala
```

<210> SEQ ID NO 4
<211> LENGTH: 30
<212> TYPE: PRT
<213> ORGANISM: Artificial sequence
<220> FEATURE:
<223> OTHER INFORMATION: Synthetic

<400> SEQUENCE: 4

```
Tyr Lys Asp Pro Leu Gly Pro Pro Arg Tyr Tyr Asn Pro Asp Lys Gly
1               5                   10                  15

Ser Arg Gly His Arg Asn Ala Glu Gln Asp Ala Ile Thr Asp
            20                  25                  30
```

<210> SEQ ID NO 5
<211> LENGTH: 27
<212> TYPE: PRT
<213> ORGANISM: Artificial sequence
<220> FEATURE:
<223> OTHER INFORMATION: Synthetic

<400> SEQUENCE: 5

```
Tyr Lys Asp Pro Leu Gly Pro Pro Arg Tyr Tyr Asn Pro Asp Lys Gly
1               5                   10                  15

Ser Arg Gly His Arg Asn Ala Glu Gln Asp Ala
            20                  25
```

<210> SEQ ID NO 6
<211> LENGTH: 27
<212> TYPE: PRT
<213> ORGANISM: Artificial sequence
<220> FEATURE:
<223> OTHER INFORMATION: Synthetic

<400> SEQUENCE: 6

```
Tyr Lys Ala Pro Leu Gly Pro Pro Arg Tyr Tyr Asn Pro Asp Lys Gly
1               5                   10                  15

Ser Arg Gly His Arg Asn Ala Glu Gln Asp Ala
            20                  25
```

<210> SEQ ID NO 7
<211> LENGTH: 27
<212> TYPE: PRT
<213> ORGANISM: Artificial sequence
<220> FEATURE:
<223> OTHER INFORMATION: Synthetic

<400> SEQUENCE: 7

```
Tyr Lys Glu Pro Leu Gly Ala Pro Arg Phe His Asn Pro Asp Lys Gly
1               5                   10                  15

Ser Arg Gly Trp Glu Asn Ala Ala Gln Asp Ala
            20                  25
```

<210> SEQ ID NO 8
<211> LENGTH: 19
<212> TYPE: PRT

```
<213> ORGANISM: Artificial sequence
<220> FEATURE:
<223> OTHER INFORMATION: Synthetic

<400> SEQUENCE: 8

Arg Tyr Tyr Asn Pro Asp Lys Gly Ser Arg Gly His Arg Asn Ala Glu
1               5                   10                  15

Gln Asp Ala


<210> SEQ ID NO 9
<211> LENGTH: 19
<212> TYPE: PRT
<213> ORGANISM: Artificial sequence
<220> FEATURE:
<223> OTHER INFORMATION: Synthetic

<400> SEQUENCE: 9

Arg Phe His Asn Pro Asp Arg Gly Ser Arg Gly Trp Lys Asn Ala Ala
1               5                   10                  15

Gln Asp Ala


<210> SEQ ID NO 10
<211> LENGTH: 18
<212> TYPE: PRT
<213> ORGANISM: Artificial sequence
<220> FEATURE:
<223> OTHER INFORMATION: Synthetic

<400> SEQUENCE: 10

Arg Phe His Asn Pro Asp Arg Gly Ser Arg Gly Trp Lys Asn Ala Ala
1               5                   10                  15

Gln Asp


<210> SEQ ID NO 11
<211> LENGTH: 19
<212> TYPE: PRT
<213> ORGANISM: Artificial sequence
<220> FEATURE:
<223> OTHER INFORMATION: Synthetic

<400> SEQUENCE: 11

Ala Asp Gln Ala Ala Asn Glu Trp Gly Arg Ser Gly Lys Asp Pro Asn
1               5                   10                  15

His Phe Arg


<210> SEQ ID NO 12
<211> LENGTH: 103
<212> TYPE: PRT
<213> ORGANISM: Mus musculis

<400> SEQUENCE: 12

Gly Phe Phe Ser Phe Ile Gly Glu Ala Phe Gln Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ser Phe
    50                  55                  60

Gln Glu Phe Phe Gly Arg Gly His Glu Asp Thr Met Ala Asp Gln Glu
65                  70                  75                  80
```

```
Ala Asn Arg His Gly Arg Ser Gly Lys Asp Pro Asn Tyr Tyr Arg Pro
                85                  90                  95

Pro Gly Leu Pro Ala Lys Tyr
            100


<210> SEQ ID NO 13
<211> LENGTH: 103
<212> TYPE: PRT
<213> ORGANISM: Artificial sequence
<220> FEATURE:
<223> OTHER INFORMATION: Synthetic

<400> SEQUENCE: 13

Tyr Lys Ala Pro Leu Gly Pro Pro Arg Tyr Tyr Asn Pro Asp Lys Gly
1               5                   10                  15

Ser Arg Gly His Arg Asn Ala Glu Gln Asp Ala Met Thr Asp Glu His
            20                  25                  30

Gly Arg Gly Phe Phe Glu Gln Phe Ser Glu Arg Ala Asp Ser Ile Lys
        35                  40                  45

Glu Ala Ala Trp Val Gly Gly Pro Gly Arg Gln Ala Ala Asp Tyr Asn
    50                  55                  60

Gly Arg Ala His Phe Tyr Lys Asp Gly Asp Lys Trp Gly Ala Glu Lys
65                  70                  75                  80

Met Asp Thr Tyr Ala Arg Trp Met Asp Gly Ala Gly Gln Phe Ala Glu
                85                  90                  95

Gly Ile Phe Ser Phe Phe Gly
            100


<210> SEQ ID NO 14
<211> LENGTH: 103
<212> TYPE: PRT
<213> ORGANISM: Mus musculis

<400> SEQUENCE: 14

Gly Phe Phe Ser Phe Ile Gly Glu Ala Phe Gln Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ser Phe
    50                  55                  60

Gln Glu Phe Phe Gly Arg Gly His Glu Asp Thr Met Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Asp Lys Tyr
            100


<210> SEQ ID NO 15
<211> LENGTH: 103
<212> TYPE: PRT
<213> ORGANISM: Mus musculis

<400> SEQUENCE: 15

Gly Phe Phe Ser Phe Ile Ser Glu Ala Phe Gln Gly Ala Gly Asp Met
1               5                   10                  15

Trp Arg Ala Tyr Thr Asp Met Arg Glu Ala Gly Trp Lys Asp Gly Asp
            20                  25                  30
```

```
Arg Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ser Phe
    50                  55                  60

Gln Glu Phe Phe Gly Arg Gly His Glu Asp Thr Met Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Ala Lys Tyr
            100


<210> SEQ ID NO 16
<211> LENGTH: 103
<212> TYPE: PRT
<213> ORGANISM: Mus musculis

<400> SEQUENCE: 16

Gly Phe Phe Ser Phe Ile Ser Glu Ala Phe Gln Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Gly Phe
    50                  55                  60

Gln Glu Phe Phe Gly Arg Gly His Glu Asp Thr Met Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Ala Lys Tyr
            100


<210> SEQ ID NO 17
<211> LENGTH: 103
<212> TYPE: PRT
<213> ORGANISM: Mus musculis

<400> SEQUENCE: 17

Gly Phe Phe Ser Phe Val His Glu Ala Phe Gln Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ser Phe
    50                  55                  60

Gln Glu Phe Phe Gly Arg Gly His Glu Asp Thr Met Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Ala Lys Tyr
            100


<210> SEQ ID NO 18
<211> LENGTH: 103
<212> TYPE: PRT
<213> ORGANISM: Mus musculis
```

```
<400> SEQUENCE: 18

Gly Phe Phe Ser Phe Ile Gly Glu Ala Phe Gln Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ser Phe
    50                  55                  60

Gln Glu Phe Phe Gly Arg Gly His Glu Asp Thr Met Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Asp Lys Tyr
            100


<210> SEQ ID NO 19
<211> LENGTH: 103
<212> TYPE: PRT
<213> ORGANISM: Mus musculis

<400> SEQUENCE: 19

Gly Phe Phe Ser Phe Val His Glu Ala Phe Gln Gly Ala Gly Asp Met
1               5                   10                  15

Trp Arg Ala Tyr Thr Asp Met Lys Glu Ala Asn Trp Lys Asn Ser Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Gly Arg Glu Ala Phe
    50                  55                  60

Gln Glu Phe Phe Gly Arg Gly His Glu Asp Thr Ile Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Asp Lys Tyr
            100


<210> SEQ ID NO 20
<211> LENGTH: 103
<212> TYPE: PRT
<213> ORGANISM: Mus musculis

<400> SEQUENCE: 20

Gly Phe Phe Ser Phe Val His Glu Ala Phe Leu Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ala Phe
    50                  55                  60

Gln Glu Phe Phe Gly Arg Gly His Glu Asp Thr Met Ala Asp Gln Glu
65                  70                  75                  80

Ala Asn Arg His Gly Arg Ser Gly Lys Asp Pro Asn Tyr Tyr Arg Pro
                85                  90                  95
```

-continued

```
Pro Gly Leu Pro Asp Lys Tyr
            100


<210> SEQ ID NO 21
<211> LENGTH: 104
<212> TYPE: PRT
<213> ORGANISM: Mus musculis

<400> SEQUENCE: 21

Gln Arg Trp Val Gln Phe Met Lys Glu Ala Gly Gln Gly Ser Arg Asp
1               5                   10                  15

Met Trp Arg Ala Tyr Ser Asp Met Lys Lys Ala Gly Trp Lys Asp Ser
            20                  25                  30

Asp Lys Tyr Phe His Ala Arg Gly Asn Tyr Asp Ala Ala Arg Arg Gly
        35                  40                  45

Pro Gly Gly Ala Trp Ala Ala Lys Val Ile Ser Asp Ala Arg Glu Ser
    50                  55                  60

Val Gln Lys Phe Thr Gly His Gly Ala Glu Asp Ser Arg Ala Asp Gln
65                  70                  75                  80

Phe Ala Asn Glu Trp Gly Arg Ser Gly Lys Asp Pro Asn His Phe Arg
                85                  90                  95

Pro Ala Gly Leu Lys Arg Lys Tyr
            100


<210> SEQ ID NO 22
<211> LENGTH: 111
<212> TYPE: PRT
<213> ORGANISM: Mus musculis

<400> SEQUENCE: 22

Asp Phe Trp Tyr Phe Phe Arg Glu Ala Phe Gln Gly Thr Trp Asp Leu
1               5                   10                  15

Trp Arg Ala Tyr Arg Asp Asn Leu Glu Ala Asn Tyr Gln Asn Ala Asp
            20                  25                  30

Gln Tyr Phe Tyr Ala Arg Gly Asn Tyr Glu Ala Gln Gln Arg Gly Ser
        35                  40                  45

Gly Gly Ile Trp Ala Ala Lys Ile Ile Ser Thr Ser Arg Lys Tyr Phe
    50                  55                  60

Gln Gly Leu Leu Asn Arg Tyr Tyr Phe Gly Ile Arg Asn His Gly Leu
65                  70                  75                  80

Glu Thr Leu Gln Ala Thr Gln Lys Ala Glu Glu Trp Gly Arg Ser Gly
                85                  90                  95

Lys Asn Pro Asn His Phe Arg Pro Glu Gly Leu Glu Ala Phe Tyr
            100                 105                 110


<210> SEQ ID NO 23
<211> LENGTH: 104
<212> TYPE: PRT
<213> ORGANISM: Homo sapien

<400> SEQUENCE: 23

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Val Trp Ala Ala Glu Ala Ile Ser Asp Ala Arg Glu Asn
```

```
    50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100


<210> SEQ ID NO 24
<211> LENGTH: 104
<212> TYPE: PRT
<213> ORGANISM: Homo sapien

<400> SEQUENCE: 24

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Val Ile Ser Asp Ala Arg Glu Asn
    50                  55                  60

Ile Gln Arg Phe Phe Gly His Asp Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100


<210> SEQ ID NO 25
<211> LENGTH: 104
<212> TYPE: PRT
<213> ORGANISM: Homo sapien

<400> SEQUENCE: 25

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Ala Ile Ser Asp Ala Arg Glu Asn
    50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100


<210> SEQ ID NO 26
<211> LENGTH: 104
<212> TYPE: PRT
<213> ORGANISM: Homo sapien

<400> SEQUENCE: 26

Arg Ser Phe Phe Ser Phe Leu Gly Glu Ala Phe Asp Gly Ala Arg Asp
1               5                   10                  15
```

```
Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Val Ile Ser Asn Ala Arg Glu Asn
    50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100


<210> SEQ ID NO 27
<211> LENGTH: 104
<212> TYPE: PRT
<213> ORGANISM: Homo sapien

<400> SEQUENCE: 27

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Val Ile Ser Asp Ala Arg Glu Asn
    50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100


<210> SEQ ID NO 28
<211> LENGTH: 104
<212> TYPE: PRT
<213> ORGANISM: Homo sapien

<400> SEQUENCE: 28

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Val Ile Ser Asn Ala Arg Glu Asn
    50                  55                  60

Ile Gln Arg Leu Thr Gly His Gly Ala Glu Asp Ser Leu Ala Asp Gln
65                  70                  75                  80

Ala Ala Asn Lys Trp Gly Arg Ser Gly Arg Asp Pro Asn His Phe Arg
                85                  90                  95

Pro Ala Gly Leu Pro Glu Lys Tyr
            100


<210> SEQ ID NO 29
```

```
<211> LENGTH: 104
<212> TYPE: PRT
<213> ORGANISM: Homo sapien

<400> SEQUENCE: 29

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Val Ile Ser Asn Ala Arg Glu Asn
    50                  55                  60

Ile Gln Arg Leu Thr Gly Arg Gly Ala Glu Asp Ser Leu Ala Asp Gln
65                  70                  75                  80

Ala Ala Asn Lys Trp Gly Arg Ser Gly Arg Asp Pro Asn His Phe Arg
                85                  90                  95

Pro Ala Gly Leu Pro Glu Lys Tyr
            100


<210> SEQ ID NO 30
<211> LENGTH: 112
<212> TYPE: PRT
<213> ORGANISM: Homo sapien

<400> SEQUENCE: 30

Glu Ser Trp Arg Ser Phe Phe Lys Glu Ala Leu Gln Gly Val Gly Asp
1               5                   10                  15

Met Gly Arg Ala Tyr Met Asp Ile Met Ile Ser Met His Gln Asn Ser
            20                  25                  30

Asn Arg Tyr Leu Tyr Ala Arg Gly Asn Tyr Asp Ala Ala Gln Arg Gly
        35                  40                  45

Pro Gly Gly Val Trp Ala Ala Lys Leu Ile Ser Arg Ser Arg Val Tyr
    50                  55                  60

Leu Gln Gly Leu Asp Tyr Tyr Leu Phe Gly Asn Ser Ile Ser Thr Val
65                  70                  75                  80

Leu Glu Asp Ser Lys Ser Asn Glu Lys Ala Glu Glu Trp Gly Arg Ser
                85                  90                  95

Gly Lys Asp Pro Asp Arg Phe Arg Pro Asp Gly Leu Pro Lys Lys Tyr
            100                 105                 110
```